(12) United States Patent
Esposito et al.

(10) Patent No.: US 9,169,255 B2
(45) Date of Patent: Oct. 27, 2015

(54) CAFFEINATED COMPOUNDS AND COMPOSITIONS FOR TREATMENT OF AMYLOID DISEASES AND SYNUCLEINOPATHIES

(71) Applicant: ProteoTech Inc, Kirkland, WA (US)

(72) Inventors: Luke Esposito, Seattle, WA (US); Kelsey Hanson, Seattle, WA (US); Marisa C. Yadon, Berea (ZA); Thomas Lake, Snohomish, WA (US); Alan D. Snow, Lynnwood, WA (US); Joel Cummings, Seattle, WA (US); Anil Kumar, Puyallup, WA (US)

(73) Assignee: Proteo Tech Inc., Kirkland, WA (US)

( * ) Notice: Subject to any disclaimer, the term of this patent is extended or adjusted under 35 U.S.C. 154(b) by 0 days.

(21) Appl. No.: 14/238,755

(22) PCT Filed: Oct. 10, 2012

(86) PCT No.: PCT/US2012/059481
§ 371 (c)(1),
(2) Date: Feb. 13, 2014

(87) PCT Pub. No.: WO2013/062762
PCT Pub. Date: May 2, 2013

(65) Prior Publication Data
US 2014/0194447 A1    Jul. 10, 2014

Related U.S. Application Data

(60) Provisional application No. 61/552,077, filed on Oct. 27, 2011.

(51) Int. Cl.
*C07D 473/12* (2006.01)
*C07D 473/04* (2006.01)
*C07D 473/06* (2006.01)
*C07D 473/08* (2006.01)
*C07D 473/10* (2006.01)

(52) U.S. Cl.
CPC ............ *C07D 473/04* (2013.01); *C07D 473/06* (2013.01); *C07D 473/08* (2013.01); *C07D 473/10* (2013.01); *C07D 473/12* (2013.01)

(58) Field of Classification Search
None
See application file for complete search history.

(56) References Cited

U.S. PATENT DOCUMENTS

| 7,514,583 | B2 | 4/2009 | Snow et al. | |
| 2005/0261316 | A1* | 11/2005 | Kalla et al. | 514/263.2 |
| 2008/0226715 | A1* | 9/2008 | Cha et al. | 424/468 |

FOREIGN PATENT DOCUMENTS

EP    1808169    * 7/2007

OTHER PUBLICATIONS

Dall'Igna, Oscar et al., "Caffeine and adenosine A2a receptor antagonists prevent B-amyloid (25-35)-induced cognitive deficits in mice." Expt. Neur. 203(2007)241-245.
Morelli, M and Simola, N. "Can dietary substances protect against Parkinson's disease? The case of caffeine." Expt Neur. 225(2010)246-249.

* cited by examiner

*Primary Examiner* — Bong-Sook Baek
(74) *Attorney, Agent, or Firm* — Rebecca Eagen

(57) ABSTRACT

Compounds and their pharmaceutically acceptable salts for treatment of β-amyloid diseases, such as observed in Alzheimer's disease and synucleinopathies, such as Parkinson's disease.

13 Claims, No Drawings

CAFFEINATED COMPOUNDS AND COMPOSITIONS FOR TREATMENT OF AMYLOID DISEASES AND SYNUCLEINOPATHIES

CROSS REFERENCE TO RELATED APPLICATIONS

This application filed under 35 U.S.C. 371 is a U.S. National Stage Application of PCT/US2012/059481 filed Oct. 10, 2012, and claims priority to U.S. Provisional Application No. 61/552,077, filed Oct. 27, 2011, each entitled "Caffeinated Compounds and Compositions for Treatment of Amyloid Diseases and Synucleinopathies", the contents of which are incorporated by reference herein.

TECHNICAL FIELD

This invention relates to compounds of the invention and pharmaceutically acceptable salts, their synthesis, pharmaceutical compositions containing them, and their use in the treatment of β amyloid diseases, such as observed in Alzheimer's disease, and synucleopathies, such as Parkinson's disease, and in the manufacture of medicaments for such treatment.

BACKGROUND OF THE INVENTION

Alzheimer's disease is characterized by the accumulation of a 39-43 amino acid peptide termed the β-amyloid protein or Aβ, in a fibrillar form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, characteristic hallmarks of Alzheimer's disease. Accumulating evidence implicates amyloid, and more specifically, the formation, deposition, accumulation and/or persistence of Aβ fibrils, as a major causative factor of Alzheimer's disease pathogenesis. In addition, besides Alzheimer's disease, a number of other amyloid diseases involve formation, deposition, accumulation and persistence of Aβ fibrils, including Down's syndrome, disorders involving congophilic angiopathy, such as but not limited to, hereditary cerebral hemorrhage of the Dutch type, and cerebral β-amyloid angiopathy.

Parkinson's disease is another human disorder characterized by the formation, deposition, accumulation and/or persistence of abnormal fibrillar protein deposits that demonstrate many of the characteristics of amyloid. In Parkinson's disease, an accumulation of cytoplasmic Lewy bodies consisting of filaments of α-synuclein are believed important in the pathogenesis and as therapeutic targets. New agents or compounds able to inhibit α-synuclein formation, deposition, accumulation and/or persistence, or disrupt pre-formed α-synuclein fibrils (or portions thereof) are regarded as potential therapeutics for the treatment of Parkinson's and related synucleopathies. A 35 amino acid fragment of α-synuclein that has the ability to form amyloid-like fibrils either in vitro or as observed in the brains of patients with Parkinson's disease. The fragment of α-synuclein is a relative important therapeutic target as this portion of α-synuclein is believed crucial for formation of Lewy bodies as observed in all patients with Parkinson's disease, synucleopathies and related disorders. In addition, the α-synuclein protein which forms fibrils, and is Congo red and Thioflavin S positive (specific stains used to detect amyloid fibrillar deposits), is found as part of Lewy bodies in the brains of patients with Parkinson's disease, Lewy body disease (Lewy in *Handbuch der Neurologie*, M. Lewandowski, ed., Springer, Berlin pp. 920-933, 1912; Pollanen et al, *J. Neuropath. Exp. Neurol.* 52:183-191, 1993; Spillantini et al, *Proc. Natl. Acad. Sci. USA* 95:6469-6473, 1998; Arai et al, *Neurosci. Lett.* 259:83-86, 1999), multiple system atrophy (Wakabayashi et al, *Acta Neuropath.* 96:445-452, 1998), dementia with Lewy bodies, and the Lewy body variant of Alzheimer's disease. In Parkinson's disease, fibrils develop in the brains of patients with this disease which are Congo red and Thioflavin S positive, and which contain predominant beta-pleated sheet secondary structure.

Amyloid as a Therapeutic Target for Alzheimer's Disease

Alzheimer's disease also puts a heavy economic burden on society. A recent study estimated that the cost of caring for one Alzheimer's disease patient with severe cognitive impairments at home or in a nursing home, is more than $47,000 per year (*A Guide to Understanding Alzheimer's Disease and Related Disorders*). For a disease that can span from 2 to 20 years, the overall cost of Alzheimer's disease to families and to society is staggering. The annual economic toll of Alzheimer's disease in the United States in terms of health care expenses and lost wages of both patients and their caregivers is estimated at $80 to $100 billion (2003 *Progress Report on Alzheimer's Disease*).

Tacrine hydrochloride ("Cognex"), the first FDA approved drug for Alzheimer's disease, is a acetylcholinesterase inhibitor (Cutler and Sramek, *N. Engl. J. Med.* 328:808 810, 1993). However, this drug has showed limited success in producing cognitive improvement in Alzheimer's disease patients and initially had major side effects such as liver toxicity. The second FDA approved drug, donepezil ("Aricept"), which is also an acetylcholinesterase inhibitor, is more effective than tacrine, by demonstrating slight cognitive improvement in Alzheimer's disease patients (Barner and Gray, *Ann. Pharmacotherapy* 32:70-77, 1998; Rogers and Friedhoff, *Eur. Neuropsych.* 8:67-75, 1998), but is not believed to be a cure. Therefore, it is clear that there is a need for more effective treatments for Alzheimer's disease patients.

Alzheimer's disease is characterized by the deposition and accumulation of a 39-43 amino acid peptide termed the beta-amyloid protein, Aβ or β/A4 (Glenner and Wong, *Biochem. Biophys. Res. Comm.* 120:885-890, 1984; Masters et al., *Proc. Natl. Acad. Sci. USA* 82:4245-4249, 1985; Husby et al., *Bull. WHO* 71:105-108, 1993). Aβ is derived by protease cleavage from larger precursor proteins termed β-amyloid precursor proteins (APPs) of which there are several alternatively spliced variants. The most abundant forms of the APPs include proteins consisting of 695, 751 and 770 amino acids (Tanzi et al., *Nature* 31:528-530, 1988).

The small Aβ peptide is a major component that makes up the amyloid deposits of "plaques" in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al., *Proc. Natl. Acad. Sci. USA* 83:4913-4917, 1986; Kosik et al., *Proc. Natl. Acad. Sci. USA* 83:4044-4048, 1986; Lee et al., *Science* 251:675-678, 1991). The pathological hallmark of Alzheimer's disease is therefore the presence of "plaques" and "tangles", with β-amyloid being deposited in the central core of the plaques. The other major type of lesion found in the Alzheimer's disease brain is the accumulation of β-amyloid in the walls of blood vessels, both within the brain parenchyma and in the walls of meningeal vessels that lie outside the brain. The β-amyloid deposits localized to the walls of blood vessels are referred to as cerebrovascular amyloid or congophilic angiopathy (Mandybur, *J. Neuropath. Exp. Neurol.* 45:79-90, 1986; Pardridge et al., *J. Neurochem.* 49:1394-1401, 1987)

For many years there has been an ongoing scientific debate as to the importance of "β-amyloid" in Alzheimer's disease, and whether the "plaques" and "tangles" characteristic of this disease were a cause or merely a consequence of the disease. Within the last few years, studies now indicate that β-amyloid is indeed a causative factor for Alzheimer's disease and should not be regarded as merely an innocent bystander. The Alzheimer's Aβ protein in cell culture has been shown to cause degeneration of nerve cells within short periods of time (Pike et al., *Br. Res.* 563:311-314, 1991; *J. Neurochem.* 64:253-265, 1995). Studies suggest that it is the fibrillar structure (consisting of a predominant β-pleated sheet secondary structure), which is responsible for the neurotoxic effects. Aβ has also been found to be neurotoxic in slice cultures of hippocampus (Harrigan et al., *Neurobiol. Aging* 16:779-789, 1995) and induces nerve cell death in transgenic mice (Games et al., *Nature* 373:523-527, 1995; Hsiao et al., *Science* 274:99-102, 1996). Injection of the Alzheimer's Aβ into rat brain also causes memory impairment and neuronal dysfunction (Flood et al., *Proc. Natl. Acad. Sci. USA* 88:3363-3366, 1991; *Br. Res.* 663:271-276, 1994).

Probably, the most convincing evidence that Aβ amyloid is directly involved in the pathogenesis of Alzheimer's disease comes from genetic studies. It was discovered that the production of Aβ can result from mutations in the gene encoding, its precursor, β-amyloid precursor protein (Van Broeckhoven et al., *Science* 248:1120-1122, 1990; Murrell et al., *Science* 254:97-99, 1991; Haass et al., *Nature Med.* 1:1291-1296, 1995). The identification of mutations in the beta-amyloid precursor protein gene that cause early onset familial Alzheimer's disease is the strongest argument that amyloid is central to the pathogenetic process underlying this disease. Four reported disease-causing mutations have been discovered which demonstrate the importance of Aβ in causing familial Alzheimer's disease (reviewed in Hardy, *Nature Genet.* 1:233-234, 1992). All of these studies suggest that providing a drug to reduce, eliminate or prevent fibrillar Aβ formation, deposition, accumulation and/or persistence in the brains of human patients will serve as an effective therapeutic.

A variety of other human diseases also demonstrate amyloid deposition and usually involve systemic organs (i.e. organs or tissues lying outside the central nervous system), with the amyloid accumulation leading to organ dysfunction or failure. These amyloid diseases (discussed below) leading to marked amyloid accumulation in a number of different organs and tissues, are known as systemic amyloidoses. In other amyloid diseases, single organs may be affected such as the pancreas in 90% of patients with type 2 diabetes. In this type of amyloid disease, the beta-cells in the islets of Langerhans in pancreas are believed to be destroyed by the accumulation of fibrillar amyloid deposits consisting primarily of a protein known as islet amyloid polypeptide (IAPP). Inhibiting or reducing such IAPP amyloid fibril formation, deposition, accumulation and persistence is believed to lead to new effective treatments for type 2 diabetes. In Alzheimer's disease, Parkinson's and "systemic" amyloid diseases, there is currently no cure or effective treatment, and the patient usually dies within 3 to 10 years from disease onset.

The amyloid diseases (amyloidoses) are classified according to the type of amyloid protein present as well as the underlying disease. Amyloid diseases have a number of common characteristics including each amyloid consisting of a unique type of amyloid protein. The amyloid diseases include, but are not limited to, the amyloid associated with Alzheimer's disease, Down's syndrome, hereditary cerebral hemorrhage with amyloidosis of the Dutch type, dementia pugilistica, inclusion body myositosis (Askanas et al, *Ann. Neurol.* 43:521-560, 1993) and mild cognitive impairment (where the specific amyloid is referred to as beta-amyloid protein or Aβ), the amyloid associated with chronic inflammation, various forms of malignancy and Familial Mediterranean Fever (where the specific amyloid is referred to as AA amyloid or inflammation-associated amyloidosis) (also known as systemic AA amyloidosis), the amyloid associated with multiple myeloma and other B-cell dyscrasias (where the specific amyloid is referred to as AL amyloid), the amyloid associated with type 2 diabetes (where the specific amyloid protein is referred to as amylin or islet amyloid polypeptide or IAPP), the amyloid associated with the prion diseases including Creutzfeldt-Jakob disease, Gerstmann-Straussler syndrome, kuru and animal scrapie (where the specific amyloid is referred to as PrP amyloid), the amyloid associated with long-term hemodialysis and carpal tunnel syndrome (where the specific amyloid is referred to as $\alpha_2$-microglobulin amyloid), the amyloid associated with senile cardiac amyloidosis and Familial Amyloidotic Polyneuropathy (where the specific amyloid is referred to as transthyretin or prealbumin), and the amyloid associated with endocrine tumors such as medullary carcinoma of the thyroid (where the specific amyloid is referred to as variants of procalcitonin). In addition, the α-synuclein protein which forms amyloid-like fibrils, and is Congo red and Thioflavin S positive (specific stains used to detect amyloid fibrillar deposits), is found as part of Lewy bodies in the brains of patients with Parkinson's disease, Lewy body disease (Lewy in *Handbuch der Neurologic*, M. Lewandowski, ed., Springer, Berlin pp. 920-933, 1912; Pollanen et al, *J. Neuropath. Exp. Neurol.* 52:183-191, 1993; Spillantini et al, *Proc. Natl. Acad. Sci. USA* 95:6469-6473, 1998; Arai et al, *Neurosci. Lett.* 259:83-86, 1999), multiple system atrophy (Wakabayashi et al, *Acta Neuropath.* 96:445-452, 1998), dementia with Lewy bodies, and the Lewy body variant of Alzheimer's disease. For purposes of this disclosure, Parkinson's disease, due to the fact that fibrils develop in the brains of patients with this disease (which are Congo red and Thioflavin S positive, and which contain predominant beta-pleated sheet secondary structure), is now regarded as a disease that also displays the characteristics of an amyloid-like disease.

Systemic amyloidoses which include the amyloid associated with chronic inflammation, various forms of malignancy and familial Mediterranean fever (i.e. AA amyloid or inflammation-associated amyloidosis) (Benson and Cohen, *Arth. Rheum.* 22:36-42, 1979; Kamei et al, *Acta Path. Jpn.* 32:123-133, 1982; McAdam et al., *Lancet* 2:572-573, 1975; Metaxas, *Kidney Int.* 20:676-685, 1981), and the amyloid associated with multiple myeloma and other B-cell dyscrasias (i.e. AL amyloid) (Harada et al., *J. Histochem. Cytochem.* 19:1-15, 1971), as examples, are known to involve amyloid deposition in a variety of different organs and tissues generally lying outside the central nervous system. Amyloid deposition in these diseases may occur, for example, in liver, heart, spleen, gastrointestinal tract, kidney, skin, and/or lungs (Johnson et al, *N. Engl. J. Med.* 321:513-518, 1989). For most of these amyloidoses, there is no apparent cure or effective treatment and the consequences of amyloid deposition can be detrimental to the patient. For example, amyloid deposition in the kidney may lead to renal failure, whereas amyloid deposition in the heart may lead to heart failure. For these patients, amyloid accumulation in systemic organs leads to eventual death generally within 3-5 years. Other amyloidoses may affect a single organ or tissue such as observed with the Aβ amyloid deposits found in the brains of patients with Alzheimer's disease and Down's syndrome: the PrP amyloid deposits found in the brains of patients with Creutzfeldt-Jakob disease, Gerstmann-Straussler syndrome, and kuru; the islet amyloid (IAPP) deposits found in the islets of Langerhans in the pancreas of 90% of patients with type 2 diabetes (Johnson et al, *N. Engl. J. Med.* 321:513-518, 1989; *Lab. Invest.* 66:522 535, 1992); the $\alpha_2$-microglobulin amyloid deposits in the medial nerve leading to carpal tunnel syndrome as observed in patients undergoing long-term hemodialysis (Geyjo et al, *Biochem. Biophys. Res. Comm.* 129:701-706, 1985; *Kidney Int.* 30:385-390, 1986); the prealbumin/transthyretin amyloid observed in the hearts of patients with senile cardiac amyloid; and the prealbumin/transthyretin amyloid observed in peripheral nerves of patients who have familial amyloidotic polyneuropathy (Skinner and Cohen, *Biochem. Biophys. Res. Comm.* 99:1326-1332, 1981; Saraiva et al, *J. Lab. Clin. Med.* 102:590-603, 1983; *J. Clin. Invest.* 74:104-119, 1984; Tawara et al, *J. Lab. Clin. Med.* 98:811-822, 1989).

Parkinson's Disease and Synucleopathies

Parkinson's disease is a neurodegenerative disorder that is pathologically characterized by the presence of intracytoplasmic Lewy bodies (Lewy in *Handbuch der Neurologie*, M. Lewandowski, ed., Springer, Berlin, pp. 920-933, 1912; Pollanen et al., *J. Neuropath. Exp. Neurol.* 52:183-191, 1993), the major components of which are filaments consisting of $\alpha$-synuclein (Spillantini et al., *Proc. Natl. Acad. Sci. USA* 95:6469-6473, 1998; Arai et al., *Neurosci. Lett.* 259:83-86, 1999), an 140-amino acid protein (Ueda et al., *Proc. Natl. Acad. Sci. USA* 90:11282-11286, 1993). Two dominant mutations in $\alpha$-synuclein causing familial early onset Parkinson's disease have been described suggesting that Lewy bodies contribute mechanistically to the degeneration of neurons in Parkinson's disease and related disorders (Polymeropoulos et al., *Science* 276:2045-2047, 1997; Kruger et al., *Nature Genet.* 18:106-108, 1998). Recently, in vitro studies have demonstrated that recombinant $\alpha$-synuclein can indeed form Lewy body-like fibrils (Conway et al., *Nature Med.* 4:1318-1320, 1998; Hashimoto et al., *Brain Res.* 799:301-306, 1998; Nahri et al., *J. Biol. Chem.* 274:9843-9846, 1999). Most importantly, both Parkinson's disease-linked $\alpha$-synuclein mutations accelerate this aggregation process, demonstrating that such in vitro studies may have relevance for Parkinson's disease pathogenesis. Alpha-synuclein aggregation and fibril formation fulfills the criteria of a nucleation-dependent polymerization process (Wood et al., *J. Biol. Chem.* 274:19509-19512, 1999). In this regard $\alpha$-synuclein fibril formation resembles that of Alzheimer's $\beta$-amyloid protein (A$\beta$) fibrils. Alpha-synuclein recombinant protein, and non-A$\beta$ component (known as NAC), which is a 35-amino acid peptide fragment of $\alpha$-synuclein, both have the ability to form fibrils when incubated at 37° C., and are positive with amyloid stains such as Congo red (demonstrating a red/green birefringence when viewed under polarized light) and Thioflavin S (demonstrating positive fluorescence) (Hashimoto et al., *Brain Res.* 799:301-306, 1998; Ueda et al., *Proc. Natl. Acad. Sci. USA* 90:11282-11286, 1993).

Synucleins are a family of small, presynaptic neuronal proteins composed of $\alpha$-, $\beta$-, and $\gamma$-synucleins, of which only $\alpha$-synuclein aggregates have been associated with several neurological diseases (Ian et al., *Clinical Neurosc. Res.* 1:445-455, 2001; Trojanowski and Lee, *Neurotoxicology* 23:457-460, 2002). The role of synucleins (and in particular, alpha-synuclein) in the etiology of a number of neurodegenerative diseases has developed from several observations. Pathologically, synuclein was identified as a major component of Lewy bodies, the hallmark inclusions of Parkinson's disease, and a fragment thereof was isolated from amyloid plaques of a different neurological disease, Alzheimer's disease. Biochemically, recombinant $\alpha$-synuclein was shown to form fibrils that recapitulated the ultrastructural features of alpha-synuclein isolated from patients with dementia with Lewy bodies, Parkinson's disease and multiple system atrophy. Additionally, the identification of mutations within the synuclein gene, albeit in rare cases of familial Parkinson's disease, demonstrated an unequivocal link between synuclein pathology and neurodegenerative diseases. The common involvement of $\alpha$-synuclein in a spectrum of diseases such as Parkinson's disease, dementia with Lewy bodies, multiple system atrophy and the Lewy body variant of Alzheimer's disease has led to the classification of these diseases under the umbrella term of "synucleopathies".

Parkinson's disease $\alpha$-synuclein fibrils, and the A$\beta$ fibrils of Alzheimer's disease, both consist of a predominantly $\beta$-pleated sheet structure. Compounds found to inhibit Alzheimer's disease A$\beta$ amyloid fibril formation have also been shown to be effective in the inhibition of $\alpha$-synuclein fibril formation, as illustrated in the Examples of the present invention. These compounds would therefore also serve as therapeutics for Parkinson's disease and other synucleopathies, in addition to having efficacy as a therapeutic for Alzheimer's disease.

Parkinson's disease and Alzheimer's disease are characterized by the inappropriate accumulation of insoluble aggregates comprised primarily of misfolded proteins that are enriched in $\beta$-pleated sheet secondary structure (reviewed in Cohen et al., *Nature* 426:905-909, 2003; Chiti et al., *Annu. Rev. Biochem.*, 75:333-366, 2006). In Parkinson's disease, $\alpha$-synuclein is the major constituent of these aggregates, as part of Lewy Bodies, and mutations in $\alpha$-synuclein that increase its propensity to misfold and aggregate are observed in familial Parkinson's disease (Polymeropoulos et al., *Science* 276:1197-1199, 1997; Papadimitriou et al., *Neurology* 52:651-654, 1999). Mitochondrial dysfunction, specifically as a result of impairment at complex I of the electron transport chain, is also a common feature of Parkinson's disease (Schapira et al., *J. Neurochem.*, 54:823-827, 1990; reviewed in Greenamyre et al., *IUBMB Life*, 52:135-141, 2001). Direct evidence for mitochondrial deficits in the etiology of Parkinson's disease came first from the observation that MPP+ (1-methyl-4-phenyl-2,3-dihydropyridinium), the active metabolite of the parkinsonism toxin N-methyl-4-phenyl-1,2,3,6-tetrahydropyridine (MPTP), inhibits complex I (Nicklas et al., *Life Sci.*, 36:2503-2508, 1985). Subsequently, rotenone, another complex I inhibitor, was shown to be an improved model for $\alpha$-synuclein aggregation because it reproduces the above-mentioned $\alpha$-synuclein-positive intracytoplasmic aggregates, in addition to the behavioral changes and loss of dopaminergic neurons seen in the MPTP model. Rotenone toxicity of this type is seen in multiple model systems including rats (Betarbet et al., *Nat. Neurosci.*, 3:1301-1306, 2000; Panov et al., *J. Biol. Chem.*, 280:42026-42035, 2005), rat brain slices (Sherer et al., *J. Neurosci.*, 23:10756-10764, 2003; Testa et al., *Mol. Brain. Res.*, 134:109-118, 2005), *C. elegans* (Ved et al., *J. Biol. Chem.*, 280:42655-42668, 2005) and cultured cells (Sherer et al., *J. Neurosci.*, 22:7006-7015, 2002) and has been shown to be a consequence of increased oxidative damage resulting from complex I inhibition. To better understand the relationship of oxidative damage to mutant $\alpha$-synuclein pathogenesis, a neuroblastoma cell line (using BE-M17 cells) has been established in the art that overexpresses A53T $\alpha$-synuclein. In these cells, A53T $\alpha$-synuclein aggregates in response to a variety of oxidative stress-inducing agents and potentiates mitochondrial dysfunction and cell death (Ostrerova-Golts et al., *J. Neurosci.*, 20:6048-6054, 2000). These cells are amenable to rotenone treatment as an oxidative stress inducer and hence, are particularly useful for testing agents that might inhibit α-synuclein aggregation/fibrillogenesis.

Discovery and identification of new compounds or agents as potential therapeutics to arrest amyloid formation, deposition, accumulation and/or persistence that occurs in Alzheimer's disease, and Parkinson's disease, are desperately sought.

SUMMARY OF THE INVENTION

This invention relates to the following compounds and other modification and derivates of these compounds and their use in the treatment of amyloid diseases and synucleopathies.

Compounds of this invention have the general formula

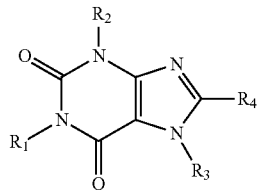

where:

$R_{1-3}$ are independently substituted with hydrogen, methyl and benzyl groups, and $R_4$ is substituted with a hydrogen or phenyl group, wherein the phenyl or benzyl groups are independently substituted with up to 2 groups selected from H, OH, F, Cl, Br, glucuronide, sulfate, cyano, methyl, $NH_2$, SH, $CH_2OH$, CN, $CF_3$, $NHSO_2CH_3$, $N(CH_3)_2$, $NHCH_3$, $N(CN)_2$, NHCN, $C(CN)_3$, $NH(C=O)NH_2$, $NH(C=O)CH_3$, $(C=NH)NH_2$, $(C=NOH)NH_2$, $O(C=O)OCH_3$, and $NH(C=O)H$ and pharmaceutically acceptable salts thereof.

Compounds of this invention have the general formula above where $R_1$ is substituted with a benzyl group, $R_2$ or $R_3$ are independently substituted with either a methyl or benzyl group and $R_4$ is substituted with a hydrogen and wherein the benzyl groups are each substituted with two hydroxyl groups.

Compounds of the invention include, but are not limited to the following:

Compound PD 150

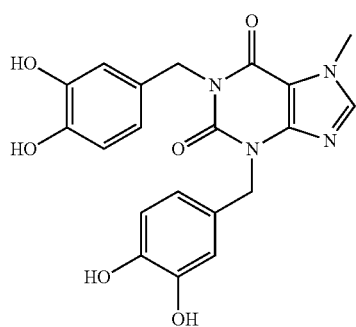

Compound PD 151

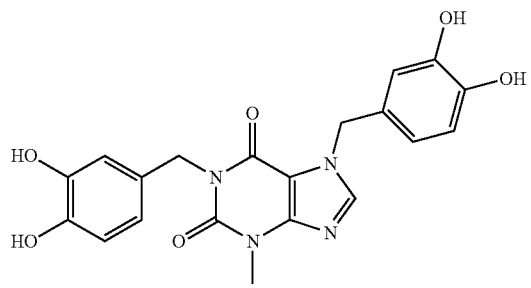

Compound PD 152

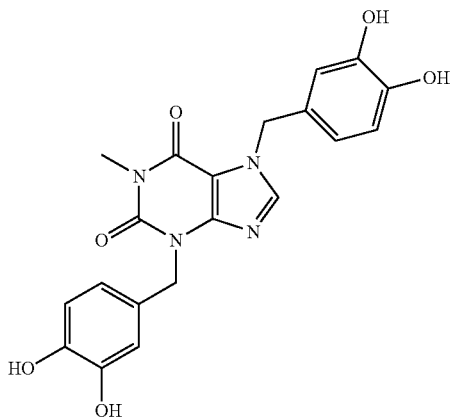

Compound PD 153

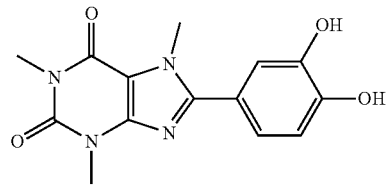

Compound PD 154

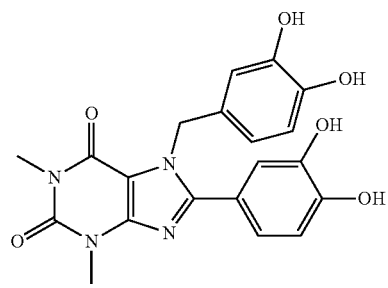

In another aspect, this invention is pharmaceutical compositions comprising a compound of this invention and a pharmaceutically acceptable excipient; and pharmaceutical compositions comprising a pharmaceutically acceptable excipient and, as the sole active ingredient, a compound of the invention.

In another aspect, this invention is a method of treating an amyloid disease or synucleopathy in a mammal, especially a human, by administration of a therapeutically effective amount of a compound of the invention, for example as a pharmaceutical composition.

In another aspect, this invention is the use of a compound of the invention in the manufacture of a medicament for the treatment of an amyloid disease or synucleopathy.

In another aspect, this invention is a method of preparation of the compounds of the invention, i.e. the compounds of the formula or list above, and/or the formation of pharmaceutically acceptable salts thereof.

In another aspect, this invention is a method of treatment of Aβ, IAPP, other amyloids, and α-synuclein or NAC fibrillogenesis, in an in vitro environment. The method includes the step of administering into the in vitro environment a therapeutically effective amount of a compound of this invention. Preferably the compound is selected from the groups described below with respect to their activity against Aβ, IAPP, and NAC.

Also provided are any pharmaceutically-acceptable derivatives, including salts, esters, enol ethers or esters, acetals, ketals, orthoesters, hemiacetals, hemiketals, solvates, hydrates or prodrugs of the compounds.

Methods using such compounds and compositions for disrupting, disaggregating and causing removal, reduction or clearance of beta amyloid or α-synuclein fibrils or aggregates are provided thereby providing new treatments for synucleopathies.

Also provided are methods for treatment, prevention or amelioration of one or more symptoms of amyloid and synuclein diseases or synucleopathies. In one embodiment, the methods inhibit or prevent amyloid or α-synuclein fibril formation, inhibit or prevent amyloid or α-synuclein fibril growth, and/or cause disassembly, disruption, and/or disaggregation of preformed amyloid or α-synuclein aggregates and amyloid or α-synuclein associated protein deposits. Amyloid diseases include, but are not limited to Alzheimer's disease, type II diabetes, systemic AA and prion diseases. Synuclein diseases include, but are not limited to Parkinson's disease, familial Parkinson's disease, Lewy body disease, dementia with Lewy bodies, multiple system atrophy, and the Parkinsonism-dementia complex of Guam.

DETAILED DESCRIPTION OF THE INVENTION

Definitions

In this application, the following terms shall have the following meanings, without regard to whether the terms are used variantly elsewhere in the literature or otherwise in the known art.

As used herein "Amyloid diseases" or "amyloidoses" are diseases associated with the formation, deposition, accumulation, or persistence of Aβ amyloid fibrils. Such diseases include, but are not limited to Alzheimer's disease, Down's syndrome, hereditary cerebral hemorrhage with amyloidosis of the Dutch type, and cerebral β-amyloid angiopathy. Other amyloid diseases such as systemic AA amyloidosis and IAPP amyloidosis of type II diabetes are also amyloid diseases.

As used herein, "Synuclein diseases" or "synucleopathies" are diseases associated with the formation, deposition, accumulation, or persistence of α-synuclein fibrils. Such diseases include, but are not limited to Parkinson's disease, familial Parkinson's disease, Lewy body disease, dementia with Lewy bodies, multiple system atrophy, and the Parkinsonism-dementia complex of Guam.

"Fibrillogenesis" refers to the formation, deposition, accumulation and/or persistence of β-amyloid fibrils, filaments, inclusions, deposits, as well as α-synuclein fibrils, filaments, inclusions, deposits or the like.

"Inhibition of fibrillogenesis" refers to the inhibition of formation, deposition, accumulation and/or persistence of such a β-amyloid fibrils or α-synuclein fibril-like deposits.

"Disruption of fibrils or fibrillogenesis" refers to the disruption of pre-formed β-amyloid or α-synuclein fibrils, that usually exist in a pre-dominant β-pleated sheet secondary structure. Such disruption by compounds provided herein may involve marked reduction or disassembly of amyloid or synuclein fibrils as assessed by various methods such as Thioflavin T fluorometry, Congo red binding, circular dichroism spectra, thioflavin S and cell based assays such as α-synuclein aggregation and XTT cytotoxicity assays and as demonstrated by the Examples presented in this application.

"Neuroprotection" or "neuroprotective" refers to the ability of a compound to protect, reduce, alleviate, ameliorate, and/or attenuate damage to nerve cells (neurodegeneration).

"Mammal" includes both humans and non-human mammals, such as companion animals (cats, dogs, and the like), laboratory animals (such as mice, rats, guinea pigs, and the like) and farm animals (cattle, horses, sheep, goats, swine, and the like).

"Pharmaceutically acceptable excipient" means an excipient that is conventionally useful in preparing a pharmaceutical composition that is generally safe, non-toxic, and desirable, and includes excipients that are acceptable for veterinary use or for human pharmaceutical use. Such excipients may be solid, liquid, semisolid, or, in the case of an aerosol composition, gaseous.

A "therapeutically effective amount" means the amount that, when administered to a subject or animal for treating a disease, is sufficient to affect the desired degree of treatment, prevention or symptom amelioration for the disease. A "therapeutically effective amount" or a "therapeutically effective dosage" in certain embodiments inhibits, reduces, disrupts, disassembles β-amyloid or α-synuclein fibril formation, deposition, accumulation and/or persistence, or treats, prevents, or ameliorates one or more symptoms of a disease associated with these conditions, such as an amyloid disease or a synucleinopathy, in a measurable amount in one embodiment, by at least 20%, in other embodiment, by at least 40%, in other embodiment by at least 60%, and in still other embodiment by at least 80%, relative to an untreated subject. Effective amounts of a compound provided herein or composition thereof for treatment of a mammalian subject are about 0.1 to about 1000 mg/Kg of body weight of the subject/day, such as from about 1 to about 100 mg/Kg/day, in other embodiment, from about 10 to about 500 mg/Kg/day. A broad range of disclosed composition dosages are believed to be both safe and effective.

The term "sustained release component" is defined herein as a compound or compounds, including, but not limited to, polymers, polymer matrices, gels, permeable membranes, liposomes, microspheres, or the like, or a combination thereof, that facilitates the sustained release of the active ingredient.

If the complex is water-soluble, it may be formulated in an appropriate buffer, for example, phosphate buffered saline, or other physiologically compatible solutions. Alternatively, if the resulting complex has poor solubility in aqueous solvents, then it may be formulated with a non-ionic surfactant such as Tween, or polyethylene glycol. Thus, the compounds and their physiological solvents may be formulated for administration by inhalation or insufflation (either through the mouth or the nose) or oral, buccal, parenteral, or rectal administration, as examples.

As used herein, pharmaceutically acceptable derivatives of a compound include salts, esters, enol ethers, enol esters, acetals, ketals, orthoesters, hemiacetals, hemiketals, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment of a disease also includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease), such as by disruption of pre-formed β-amyloid or α-synuclein fibrils. As used herein, amelioration of the symptoms of a particular disorder by administration of a particular compound or pharmaceutical composition refers to any lessening, whether permanent or temporary, lasting or transient that can be attributed to or associated with administration of the composition.

As used herein, inhibition of α-synuclein fibril formation, deposition, accumulation, aggregation, and/or persistence is believed to be effective treatment for a number of diseases involving α-synuclein, such as Parkinson's disease, Lewy body disease and multiple system atrophy.

As used herein, inhibition of amyloid fibril formation, deposition, accumulation, aggregation, and/or persistence is believed to be effective treatment for a number of diseases involving amyloid, such as Alzheimer's disease, type II diabetes and systemic AA amyloidosis.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

Chemical structures for some of the compounds of this invention are shown. The names of the compounds are variously IUPAC names [names derived according to the accepted IUPAC (International Union of Pure and Applied Chemistry) system established by the coalition of the Commission on Nomenclature of Organic Chemistry and the Commission on Physical Organic Chemistry, as can be found at http://www.chem.qmul.ac.uk/iupac], names derived from IUPAC names by addition or substitution (for example, by the use of "3,4-methylenedioxyphenyl" derived from "phenyl" instead of "benzo[1,3]dioxol-5-yl"), and names derived from the names of reactants. However, the names used are explicitly equated to chemical structures, and are believed to be readily understood by a person of ordinary skill in the art.

"A pharmaceutical agent" or "pharmacological agent" or "pharmaceutical composition" refers to a compound or combination of compounds used for treatment, preferably in a pure or near pure form. In the specification, pharmaceutical or pharmacological agents include the compounds of this invention. The compounds are desirably purified to 80% homogeneity, and preferably to 90% homogeneity. Compounds and compositions purified to 99.9% homogeneity are believed to be advantageous. As a test or confirmation, a suitable homogeneous compound on HPLC would yield, what those skilled in the art would identify as a single sharp-peak band.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

Compounds of the Invention

The compounds of this invention have the general formula

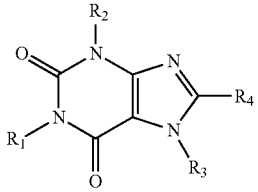

where:

$R_{1-3}$ are independently substituted with hydrogen, methyl and benzyl groups, and $R_4$ is substituted with a hydrogen, or phenyl group, wherein the phenyl or benzyl groups are independently substituted with up to 2 groups selected from H, OH, F, Cl, Br, glucuronide, sulfate, cyano, methyl, $NH_2$, SH, $CH_2OH$, CN, $CF_3$, $NHSO_2CH_3$, $N(CH_3)_2$, $NHCH_3$, $N(CN)_2$, NHCN, $C(CN)_3$, $NH(C=O)NH_2$, $NH(C=O)CH_3$, $(C=NH)NH_2$, $(C=NOH)NH_2$, $O(C=O)OCH_3$, and $NH(C=O)H$ and pharmaceutically acceptable salts thereof.

The compounds of this invention are selected from the group consisting of:

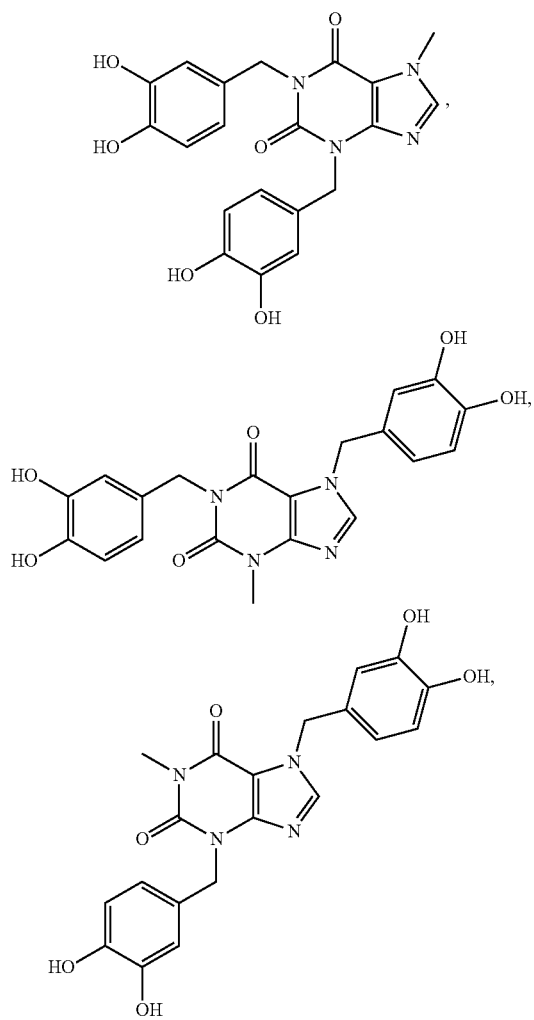

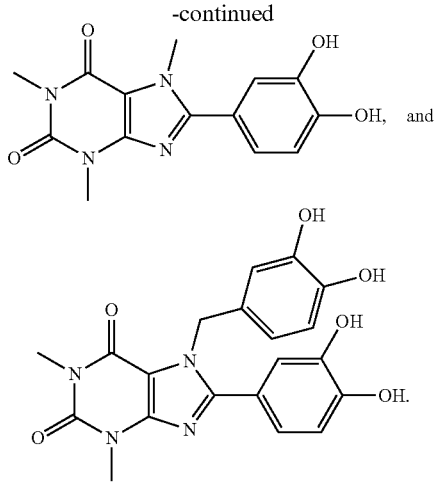

The compounds of this invention have the formula shown above where $R_1$ is substituted with a benzyl group, $R_2$ or $R_3$ are independently substituted with either a methyl or benzyl group and $R_4$ is substituted with a hydrogen and wherein the benzyl groups are each substituted with two hydroxyl groups.

The compounds of this invention are incorporated into pharmaceutical compositions comprising any of the compounds of this invention disclosed herein and a pharmaceutically acceptable excipient.

This invention also provides a method of treating the formation, deposition, accumulation, or persistence of amyloid or α-synuclein fibrils, comprising treating the fibrils with an effective amount of any of the compounds of this invention disclosed herein.

This invention also provides a method of treating an amyloid disease or a synucleinopathy in a mammal suffering therefrom, comprising administration of a therapeutically effective amount of any of the compounds of this invention disclosed herein.

This invention provides that the amyloid disease is selected from the group of diseases consisting of Alzheimer's disease, type II diabetes, systemic AA amyloidosis, Down's syndrome, hereditary cerebral hemorrhage with amyloidosis of the Dutch type, and cerebral β-amyloid angiopathy.

This invention provides that the amyloid disease is Alzheimer's disease.

This invention provides that the synucleinopathy is selected from the group consisting of Parkinson's disease, familial Parkinson's disease, and Lewy body disease, the Lewy body variant of Alzheimer's disease, dementia with Lewy bodies, multiple system atrophy, and the Parkinsonism-dementia complex of Guam.

This invention provides that the synucleinopathy is Parkinson's disease.

This invention provides that in the methods of treating an amyloid disease or a synucleinopathy that the compounds of this invention are administered in an amount between 0.1 mg/Kg/day and 1000 mg/Kg/day.

This invention provides that in the methods of treating an amyloid disease or a synucleinopathy that the compounds of this invention are administered in an amount between 1 mg/Kg/day and 100 mg/Kg/day.

This invention provides that in the methods of treating an amyloid disease or a synucleinopathy that the compounds of this invention are administered in an amount between 10 mg/Kg/day and 100 mg/Kg/day.

This invention also provides an article of manufacture, comprising packaging material, the compounds of this invention, or a pharmaceutically acceptable salts thereof, contained within packaging material, which is used for treating the formation, deposition, accumulation, or persistence of β-amyloid or α-synuclein fibrils and/or aggregates, and a label that indicates that the compound or pharmaceutically acceptable salt thereof is used for treating the formation, deposition, accumulation, or persistence of β-amyloid or α-synuclein fibrils and/or aggregates.

The compounds of this invention are compounds selected from but not limited to:

Compound PD 150

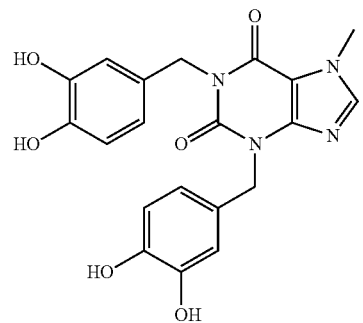

Compound PD 151

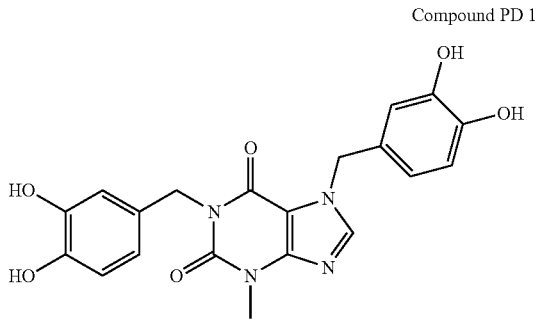

Compound PD 152

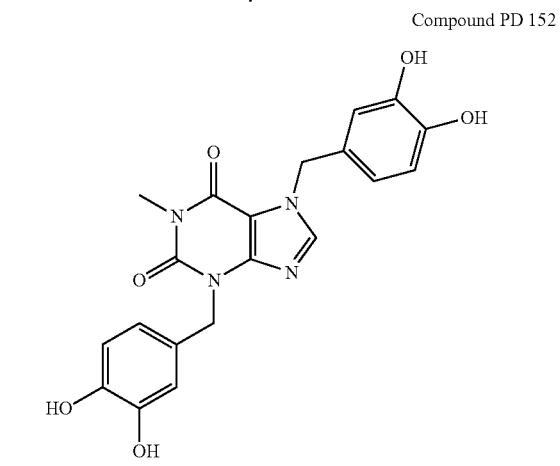

Compound PD 153

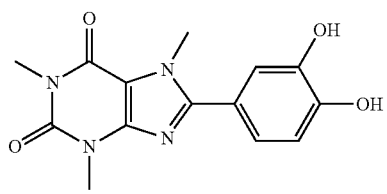

Compound PD 154

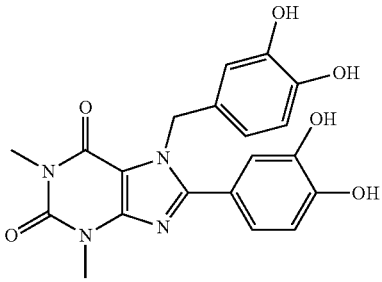

Synthesis of the Compounds of the Invention

The compounds of this invention may be prepared by methods generally known to the person of ordinary skill in the art, having regard to that knowledge and the disclosure of this application including Example 1.

The starting materials and reagents used in preparing these compounds are either available from commercial suppliers such as the Aldrich Chemical Company (Milwaukee, Wis.), Bachem (Torrance, Calif.), Sigma (St. Louis, Mo.), or Lancaster Synthesis Inc. (Windham, N.H.) or are prepared by methods well known to a person of ordinary skill in the art, following procedures described in such references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In most cases, protective groups for the hydroxy groups are introduced and finally removed. Suitable protective groups are described in Greene et al., *Protective Groups in Organic Synthesis*, Second Edition, John Wiley and Sons, New York, 1991. Other starting materials or early intermediates may be prepared by elaboration of the materials listed above, for example, by methods well known to a person of ordinary skill in the art.

The starting materials, intermediates, and compounds of this invention may be isolated and purified using conventional techniques, including precipitation, filtration, distillation, crystallization, chromatography, and the like. The compounds may be characterized using conventional methods, including physical constants and spectroscopic methods.

Pharmacology and Utility

The compounds provided herein can be used as such, be administered in the form of pharmaceutically acceptable salts derived from inorganic or organic acids, or used in combination with one or more pharmaceutically acceptable excipients. The phrase "pharmaceutically acceptable salt" means those salts which are, within the scope of sound medical judgment, suitable for use in contact with the tissues without undue toxicity, irritation, allergic response, and the like, and are commensurate with a reasonable benefit/risk ratio. Pharmaceutically acceptable salts are well known in the art. The salts can be prepared either in situ during the final isolation and purification of the compounds provided herein or separately by reacting the acidic or basic drug substance with a suitable base or acid respectively. Typical salts derived from organic or inorganic acids salts include, but are not limited to hydrochloride, hydrobromide, hydroiodide, acetate, adipate, alginate, citrate, aspartate, benzoate, bisulfate, gluconate, fumarate, hydroiodide, lactate, maleate, oxalate, palmitoate, pectinate, succinate, tartrate, phosphate, glutamate, and bicarbonate. Typical salts derived from organic or inorganic bases include, but are not limited to lithium, sodium, potassium, calcium, magnesium, ammonium, monoalkylammonium such as meglumine, dialkylammonium, trialkylammonium, and tetralkylammonium.

Actual dosage levels of active ingredients and the mode of administration of the pharmaceutical compositions provided herein can be varied in order to achieve the effective therapeutic response for a particular patient. The phrase "therapeutically effective amount" of the compound provided herein means a sufficient amount of the compound to treat disorders, at a reasonable benefit/risk ratio applicable to any medical treatment. It will be understood, however, that the total daily usage of the compounds and compositions of the provided will be decided by the attending physician within the scope of sound medical judgment. The total daily dose of the compounds provided herein may range from about 0.1 to about 1000 mg/kg/day. For purposes of oral administration, doses can be in the range from about 1 to about 500 mg/kg/day. If desired, the effective daily dose can be divided into multiple doses for purposes of administration; consequently, single dose compositions may contain such amounts or submultiples thereof to make up the daily dose. The specific therapeutically effective dose level for any particular patient will depend upon a variety of factors including the disorder being treated and the severity of the disorder; medical history of the patient, activity of the specific compound employed; the specific composition employed, age, body weight, general health, sex and diet of the patient, the time of administration, route of administration, the duration of the treatment, rate of excretion of the specific compound employed, drugs used in combination or coincidental with the specific compound employed; and the like.

The compounds provided can be formulated together with one or more non-toxic pharmaceutically acceptable diluents, carriers, adjuvants, and antibacterial and antifungal agents such as parabens, chlorobutanol, phenol, sorbic acid, and the like. Proper fluidity can be maintained, for example, by the use of coating materials such as lecithin, by the maintenance of the required particle size in the case of dispersions, and by the use of surfactants. In some cases, in order to prolong the effect of the drug, it is desirable to decrease the rate of absorption of the drug from subcutaneous or intramuscular injection. This can be accomplished by suspending crystalline or amorphous drug substance in a vehicle having poor water solubility such as oils. The rate of absorption of the drug then depends upon its rate of dissolution, which, in turn, may depend upon crystal size and crystalline form. Prolonged absorption of an injectable pharmaceutical form can be achieved by the use of absorption delaying agents such as aluminum monostearate or gelatin.

The compound provided herein can be administered enterally or parenterally in solid or liquid forms. Compositions suitable for parenteral injection may comprise physiologically acceptable, isotonic sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar and tragacanth, or mixtures of these substances.

The compounds provided herein can also be administered by injection or infusion, either subcutaneously or intravenously, or intramuscularly, or intrasternally, or intranasally, or by infusion techniques in the form of sterile injectable or oleaginous suspension. The compound may be in the form of a sterile injectable aqueous or oleaginous suspensions. These suspensions may be formulated according to the known art using suitable dispersing of wetting agents and suspending agents that have been described above. The sterile injectable preparation may also be a sterile injectable solution or suspension in a non-toxic parenterally-acceptable diluent or solvent for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oils may be conventionally employed including synthetic mono- or di-glycerides. In addition fatty acids such as oleic acid find use in the preparation of injectables. Dosage regimens can be adjusted to provide the optimum therapeutic response. For example, several divided dosages may be administered daily or the dosage may be proportionally reduced as indicated by the exigencies of the therapeutic situation.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or (a) fillers or extenders such as starches, lactose, sucrose, glucose, mannitol and silicic acid; (b) binders such as carboxymethylcellulose, alginates, gelatin, polyvinylpyrrolidone, sucrose and acacia; (c) humectants such as glycerol; (d) disintegrating agents such as agar-agar, calcium carbonate, potato or tapioca starch, alginic acid, certain silicates and sodium carbonate; (e) solution retarding agents such as paraffin; (f) absorption accelerators such as quaternary ammonium compounds; (g) wetting agents such as cetyl alcohol and glycerol monostearate; (h) absorbents such as kaolin and bentonite clay and (i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner.

Examples of embedding compositions which can be used include polymeric substances and waxes. Tablets contain the compound in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, maize starch or alginic acid; binding agents, for example, maize starch, gelatin or acacia, and lubricating agents, for example, magnesium stearate or stearic acid or talc. The tablets may be uncoated or they may be coated by known techniques to delay disintegration and absorption in the gastrointestinal tract and thereby provide a sustained action over a longer period. For example, a time delay material such as glycerol monostearate or glycerol distearate may be employed. Formulations for oral use may also be presented as hard gelatin capsules wherein the compound is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents.

Other oral delivery systems such as self-microemulsifying drug delivery systems (SMEDDS) in liquid and pellet forms that result in improved solubility, dissolution, and in vivo oral absorption of the poorly water-soluble compounds can be formulated such as those developed for curcumin. (European Journal of Pharmaceutics and Biopharmaceutics 76 (2010) 475-485)

Aqueous suspensions contain the compound in admixture with excipients suitable for the manufacture of aqueous suspensions. Such excipients are suspending agents, for example, sodium carboxymethylcellulose, methylcellulose, hydroxypropylmethyl cellulose, sodium alginate, polyvinylpyrrolidone, gum tragacanth and gum acacia; dispersing or wetting agents may be naturally occurring phosphatides, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids such as hexitol such as polyoxyethylene sorbitol monooleate, or condensation products of ethylene oxide with partial esters from fatty acids and a hexitol anhydrides, for example, polyethylene sorbitan monooleate. The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the compound in a vegetable oil, for example arachis oil, olive oil, sesame oil, or coconut oil or in a mineral oil such as liquid paraffin. The oily suspensions may contain a thickening agent, for example beeswax, hard paraffin or cetyl alcohol. Sweetening agents, such as those set forth below, and flavoring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already described above. Additional excipients, for example sweetening, flavoring and agents, may also be present.

The compounds provided herein may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean, lecithin, and occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsion may also contain sweetening and flavoring agents. Syrups and elixirs may be formulated with sweetening agents, for example, glycerol, sorbitol or sucrose. Such formulations may also contain a demulcent, a preservative and flavoring and coloring agents.

In one embodiment, the compounds are formulated in dosage unit form for ease of administration and uniformity of dosage. Dosage unit form as used herein refers to physically discrete units suited as unitary dosages for the subjects to be treated; each containing a therapeutically effective quantity of the compound and at least one pharmaceutical excipient. A drug product will comprise a dosage unit form within a container that is labeled or accompanied by a label indicating the intended method of treatment, such as the treatment of a disease associated with α-synuclein fibril formation such as Parkinson's disease. Compositions for rectal or vaginal administration are preferably suppositories which can be prepared by mixing the compounds provided herein with suitable non-irritating excipients or carriers such as cocoa butter, polyethylene glycol or a suppository wax which are solid at room temperature but liquid at body temperature and therefore melt in the rectum or vaginal cavity and release the active compound.

Compounds provided herein can also be administered in the form of liposomes. Methods to form liposomes are known in the art (Prescott, Ed., *Methods in Cell Biology* 1976, Volume XIV, Academic Press, New York, N.Y.) As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound provided herein, stabilizers, preservatives, excipients and the like. The preferred lipids are natural and synthetic phospholipids and phosphatidyl cholines (lecithins).

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Sustained Release Formulations

The invention also includes the use of sustained release formulations to deliver the compounds of the present invention to the desired target (i.e. brain or systemic organs) at high circulating levels (between $10^{-9}$ and $10^{-4}$ M) are also disclosed. In a preferred embodiment for the treatment of Parkinson's disease, the circulating levels of the compounds is maintained up to $10^{-7}$ M. The levels are either circulating in the patient systemically, or in a preferred embodiment, present in brain tissue, and in a most preferred embodiments, localized to the α-synuclein fibril deposits in brain or other tissues.

It is understood that the compound levels are maintained over a certain period of time as is desired and can be easily determined by one skilled in the art using this disclosure and compounds of the invention. In a preferred embodiment, the invention includes a unique feature of administration comprising a sustained release formulation so that a constant level of therapeutic compound is maintained between $10^{-8}$ and $10^{-6}$ M between 48 to 96 hours in the sera.

Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein, may be readily selected for use with the pharmaceutical compositions of the invention. Thus, single unit dosage forms suitable for oral administration, such as, but not limited to, tablets, capsules, gelcaps, caplets, powders and the like, that are adapted for sustained release are encompassed by the present invention.

In a preferred embodiment, the sustained release formulation contains active compound such as, but not limited to, microcrystalline cellulose, maltodextrin, ethylcellulose, and magnesium stearate. As described above, all known methods for encapsulation which are compatible with properties of the disclosed compounds are encompassed by this invention. The sustained release formulation is encapsulated by coating particles or granules of the pharmaceutical composition of the invention with varying thickness of slowly soluble polymers or by microencapsulation. In a preferred embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one preferred embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, having a relatively high percentage of plasticizer in the coating in order to permit sufficient flexibility to prevent substantial breakage during compression are disclosed. The specific amount of plasticizer varies depending on the nature of the coating and the particular plasticizer used. The amount may be readily determined empirically by testing the release characteristics of the tablets formed. If the medicament is released too quickly, then more plasticizer is used. Release characteristics are also a function of the thickness of the coating. When substantial amounts of plasticizer are used, the sustained release capacity of the coating diminishes. Thus, the thickness of the coating may be increased slightly to make up for an increase in the amount of plasticizer. Generally, the plasticizer in such an embodiment will be present in an amount of about 15 to 30% of the sustained release material in the coating, preferably 20 to 25%, and the amount of coating will be from 10 to 25% of the weight of the active material, preferably 15 to 20%. Any conventional pharmaceutically acceptable plasticizer may be incorporated into the coating.

The compounds of the invention can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations of the invention are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds. The term "sustained release component" in the context of the present invention is defined herein as a compound or compounds, including, but not limited to, polymers, polymer matrices, gels, permeable membranes, liposomes, microspheres, or the like, or a combination thereof, that facilitates the sustained release of the active ingredient.

If the complex is water-soluble, it may be formulated in an appropriate buffer, for example, phosphate buffered saline, or other physiologically compatible solutions. Alternatively, if the resulting complex has poor solubility in aqueous solvents, then it may be formulated with a non-ionic surfactant such as Tween, or polyethylene glycol. Thus, the compounds and their physiologically solvents may be formulated for administration by inhalation or insufflation (either through the mouth or the nose) or oral, buccal, parenteral, or rectal administration, as examples.

Preparations for oral administration may be suitably formulated to give controlled release of the active compound. In a preferred embodiment, the compounds of the present invention are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compounds of the invention may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachis, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and non-toxic, include but are not limited to hydrogels, silicones, polyethylenes, ethylene-vinyl acetate copolymers, or biodegradable polymers.

EXAMPLES

Example 1

Synthesis of the Compounds of the Invention

The compounds of this invention may be prepared by methods generally known to the person of ordinary skill in the art, having regard to that knowledge and the disclosure of this application including the Examples presented below.

The starting materials and reagents used in preparing these compounds are either available from commercial suppliers such as the Aldrich Chemical Company (Milwaukee, Wis.), Bachem (Torrance, Calif.), Sigma (St. Louis, Mo.), or Lancaster Synthesis Inc. (Windham, N.H.) or are prepared by methods well known to a person of ordinary skill in the art, following procedures described in such references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

3,4-(bisbenzyloxy)benzoic acid benzyl ester

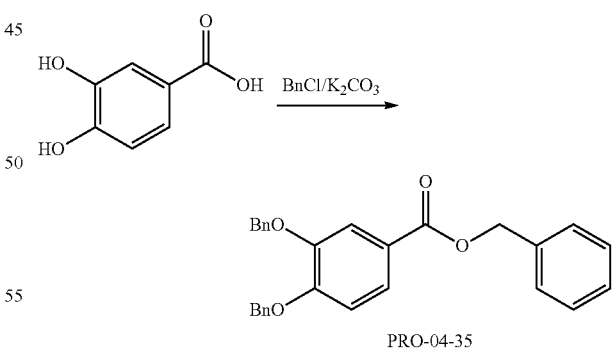

PRO-04-35

Anhydrous potassium carbonate (10.9 g, 79.5 mmol) was added to a solution of 3,4-Dihydroxybenzoic acid (3.5 g, 22.7 mmol) in anhydrous DMF (100 ml followed by benzyl chloride (8.8 g, 69.2 mmol). The resulting suspension was stirred under argon at 60° C. overnight. The reaction mixture was poured in water (150 ml) and extracted with ethyl acetate (3×50 ml). The combined organic extract was washed with water, brine solution (50 ml each) dried over anhydrous magnesium sulfate. The solvent was removed under reduced pressure. Yield=9.4 g, 98% yield. PRO-04-35.

3,4-(bisbenzyloxy)benzyl alcohol

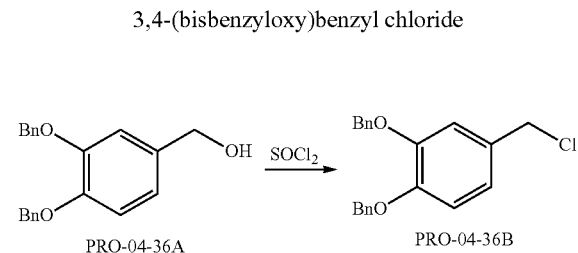

A solution of 3,4-(bisbenzyloxy)benzoic acid benzyl ester (lot # PRO-04-35, 9.0 g, 21.2 mmol) in 60 ml of anhydrous ether was added drop wise to a suspension of lithium aluminum hydride (0.89 g, 23.31 mmol) in ether (30 ml). The reaction mixture was quenched after three hours by slowly adding hydrated sodium sulfate. The reaction mixture was filtered after stifling for thirty minutes and the filtrate was concentrated under reduced pressure to yield the alcohol as a white solid. PRO-04-36A, 6.3 g, 93% yield.

3,4-(bisbenzyloxy)benzyl chloride

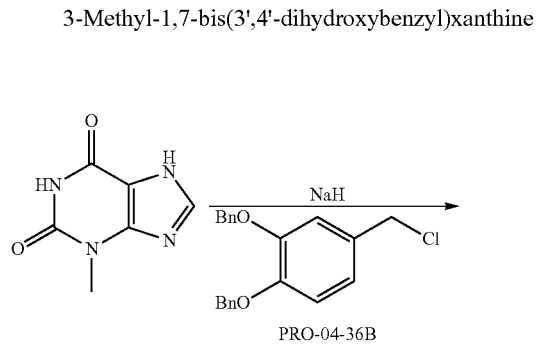

3,4-(bisbenzyloxy)benzyl alcohol (Lot #PRO-04-36A, 6.0 g, 18.7 mmol) was added to thionyl chloride (12 ml) and DMF (0.2 ml) at room temperature and the reaction mixture was heated to 60° C. for 2 hrs. Excess thionyl chloride was removed under reduced pressure. The yellow residue was dissolved in 20% ethyl acetate in hexane and was passed through a short bed of silica gel. The silica gel is flushed with 20% ethyl acetate in hexane (200 ml). The combined washing was concentrated under reduced pressure to yield the desired chloride as a yellow solid, PRO-04-36B, 5.1 g, 81% yield.

3-Methyl-1,7-bis(3',4'-dihydroxybenzyl)xanthine

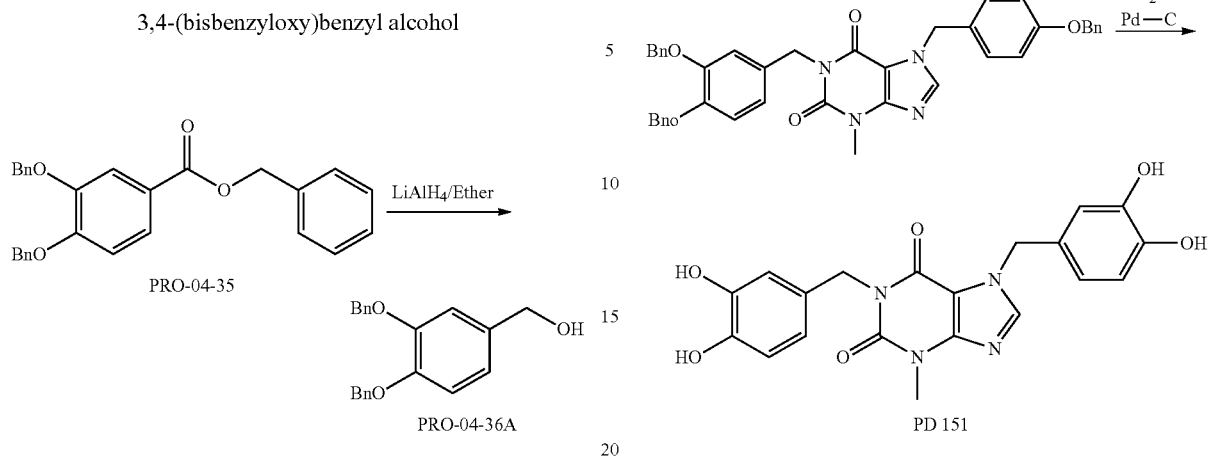

A solution of 3-methyl xanthine (200 mg, 1.2 mmol) in N,N-dimethylformamide (5 ml) was treated with 3,4-bis-benzyloxy-benzyl chloride (Lot #PRO-04-36B, 1.02 g, 3 mmol) and NaH (96 mg, 4 mmol) and 0.5 equivalent tetrabutyl ammonium iodide and was heated to 60° C. for 12 hrs. The reaction mixture was poured in water and extracted with ethyl acetate (3×30 ml). The combined organic extract was washed with water, brine solution (30 ml) each and dried over anhydrous magnesium sulfate. The solvent was removed under reduced pressure and the product was purified by flash column chromatography over silica gel using 40% ethyl acetate/hexane to yield the desired product, 600 mg, 78% yield. This product was dissolved in ethyl acetate (25 ml) and methanol (10 ml) and acetic acid (1 ml) and hydrogenated in presence of 10% Pd—C at 55 PSI for 2 hr. Catalyst was filtered off and the solvent was removed under reduced pressure. The residue was purified on a silica gel column eluting with 50% ethyl acetate in hexane to 100% ethyl acetate. The desired product was isolated as an off white solid, Yield=400 mg PD 151.

7-Methyl-1,3-bis(3',4'-dihydroxy)benzylxanthine

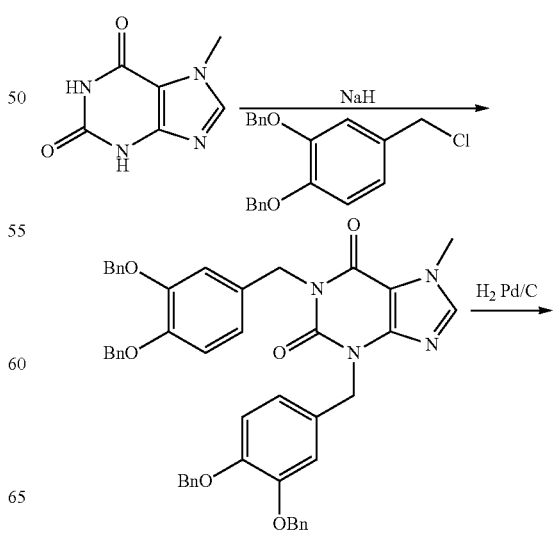

27
-continued

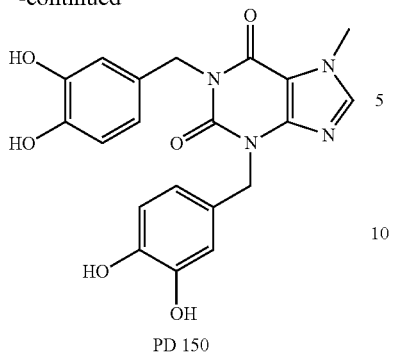
PD 150

7-Methyl-1,3-bis(3',4'-dihydroxy)benzylxanthine was synthesized from 7-methyl xanthine (200 mg, 1.2 mmol) following the general procedure as described in the previous experiment. Yield 150 mg PD 150.

1-Methyl-1,3-bis(3',4'-dihydroxy)benzyl xanthine

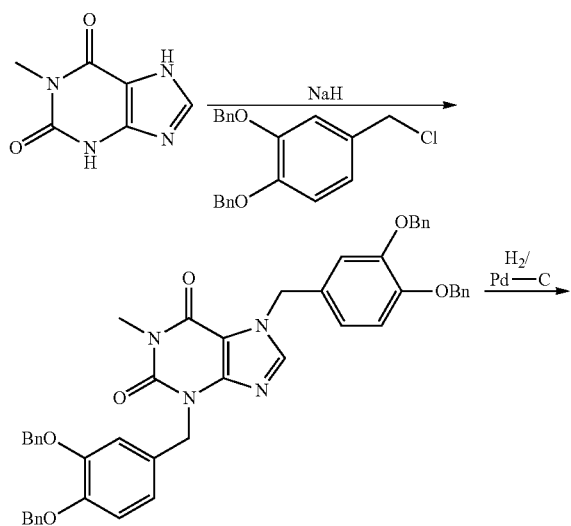

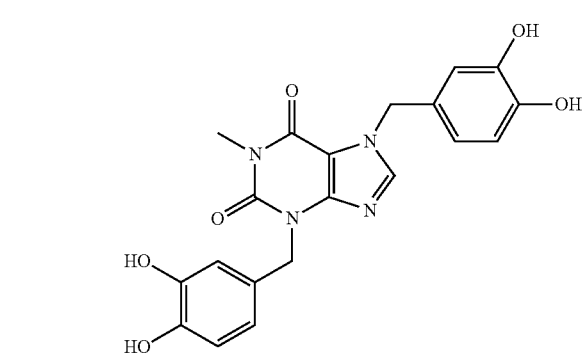
PD 152

1-Methyl-1,3-bis(3',4'-dihydroxy)benzyl xanthine was synthesized from 1-methyl xanthine (200 mg, 1.2 mmol) following the general procedure as described in the previous experiment. Yield 200 mg PD 152.

28

8-Bromo-3-Methyl-7-(3',4'-dibenzyloxy)benzyl xanthine

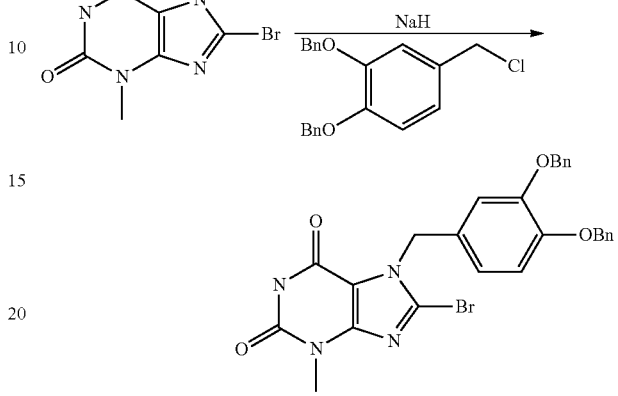

A solution of 3-methyl-8-bromo xanthine (294 mg, 1.2 mmol) in N,N-dimethylformamide (5 ml) was added to NaH (96 mg, 4 mmol) 3,4-bis-benzyloxy-benzyl chloride (Lot #PRO-04-36B, 1.02 g, 3 mmol) and tetrabutylammonium iodide (0.5 equivalent). The solution was heated to 60° C. for 12 hrs. The reaction mixture was poured in water and extracted with ethyl acetate (3×30 ml). The combined organic extract was washed with water, brine solution (30 ml) each and dried over anhydrous magnesium sulfate. The solvent was removed under reduced pressure and the product was purified by flash column chromatography over silica gel using 40% ethyl acetate/hexane to yield the desired product, 511 mg, 78% yield.

8-Bromo-1,3-dimethyl-7-(3',4'-dibenzyloxy)benzyl xanthine

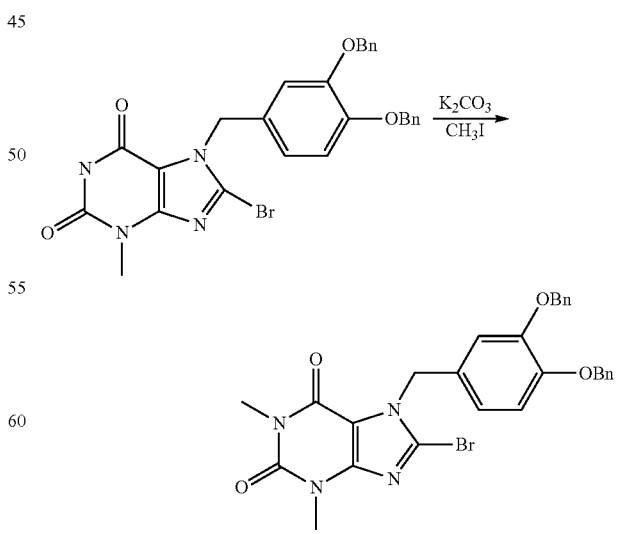
PRO-04-42

A solution of 8-Bromo-3-Methyl-7-(3',4'-dibenzyloxy) benzyl xanthine (511 mg; 0.94 mmol) and methyl iodide (426 mg; 3 mmol) in N,N-dimethylformamide (5 ml) was added to potassium carbonate (138 mg; 1.0 mmol) and was heated to 60° C. for 6 hrs. The reaction mixture was poured in water (25 ml) and extracted with ethyl acetate (3×25 ml). The combined extract was dried over anhydrous Magnesium Sulfate and concentrated under reduced pressure. The product was purified by flash chromatography over silica gel eluting with 30% ethyl acetate/hexane to yield the desired product. 535 mg, 95% PRO-04-42

1,3-dimethyl-7-(3',4'-dibenzyloxy)benzyl-8-(3',4'-dimethoxyphenyl)xanthine

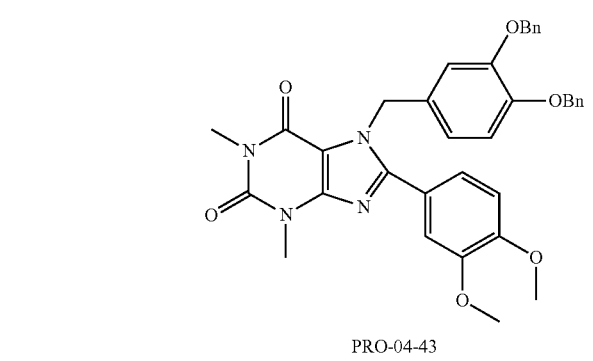

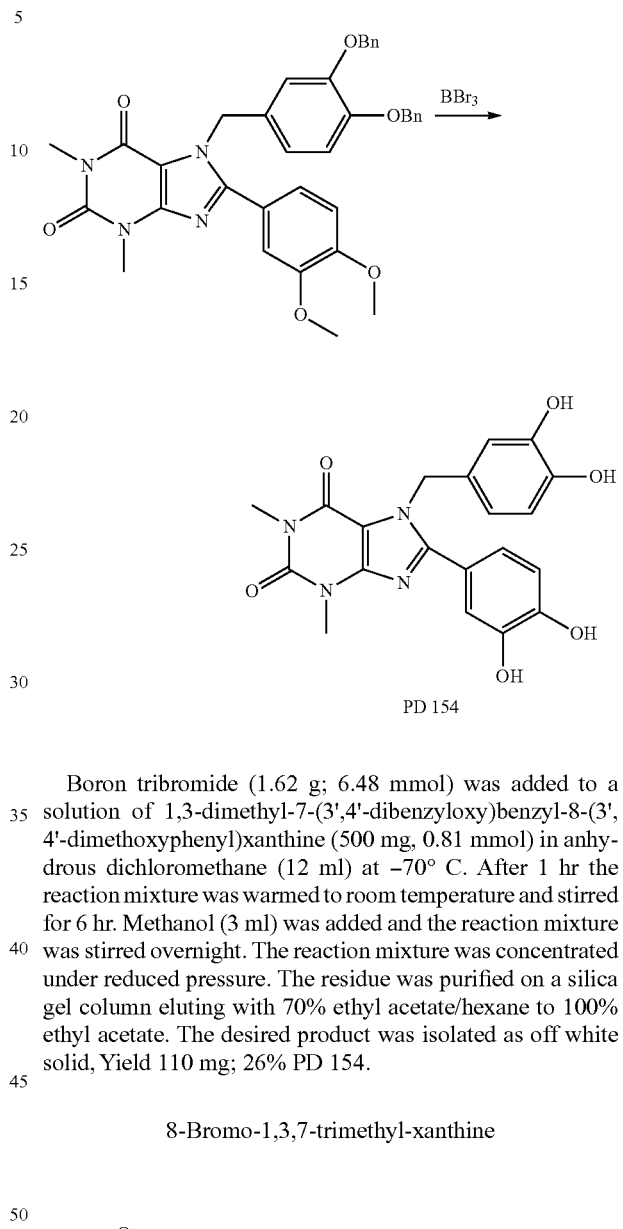

A solution of 8-Bromo-1,3-dimethyl-7-(3',4'-dibenzyloxy)benzyl xanthine (535 mg, 0.95 mmol) and 3,4-dimethoxy phenylboronic acid (182 mg; 1 mmol) in 1,4-dioxane (5 ml) was treated tetrakis(triphenyl phosphine) palladium(0) (77 mg, 0.1 mmol) and potassium carbonate (277 mg, 2 mmol). The mixture was heated to 70° C. for 12 hrs under argon atmosphere. The reaction mixture was concentrated under reduced pressure. The residue was purified on a silica gel column eluting with 40% ethyl acetate in hexane to 70% ethyl acetate. The desired product was isolated as off white solid, Yield 500 mg, 81% PRO-04-43

1,3-dimethyl-7-(3',4'-dibenzyloxy)benzyl-8-(3',4'-dihydroxyphenyl)xanthine

Boron tribromide (1.62 g; 6.48 mmol) was added to a solution of 1,3-dimethyl-7-(3',4'-dibenzyloxy)benzyl-8-(3',4'-dimethoxyphenyl)xanthine (500 mg, 0.81 mmol) in anhydrous dichloromethane (12 ml) at −70° C. After 1 hr the reaction mixture was warmed to room temperature and stirred for 6 hr. Methanol (3 ml) was added and the reaction mixture was stirred overnight. The reaction mixture was concentrated under reduced pressure. The residue was purified on a silica gel column eluting with 70% ethyl acetate/hexane to 100% ethyl acetate. The desired product was isolated as off white solid, Yield 110 mg; 26% PD 154.

8-Bromo-1,3,7-trimethyl-xanthine

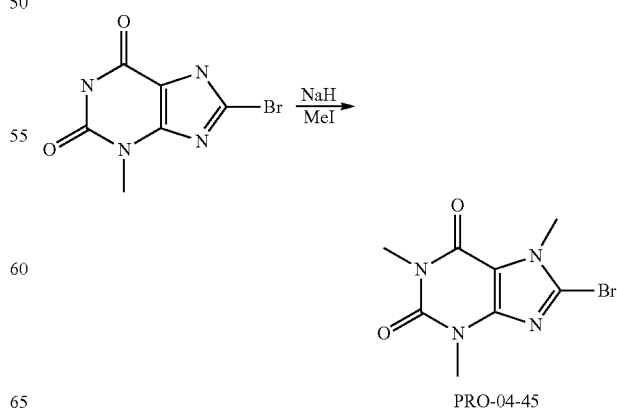

A solution of 8-bromo-3-methyl xanthine (300 mg; 1.2 mmol) and methyl iodide (1.42 g; 10.0 mmol) in N,N-dimethylformamide (5 ml) was added to potassium carbonate (662 mg; 4.8 mmol) and was heated to 60° C. for 6 hrs. The reaction mixture was poured in water (25 ml) and extracted with ethyl acetate (3×25 ml). The combined extract was dried over anhydrous magnesium sulfate and concentrated under reduced pressure. The product was purified by flash chromatography over silica gel eluting with ethyl acetate to yield the desired product. 315 mg; 92% PRO-04-45

1,3,7-trimethyl-8-(3',4'-dimethoxyphenyl)xanthine

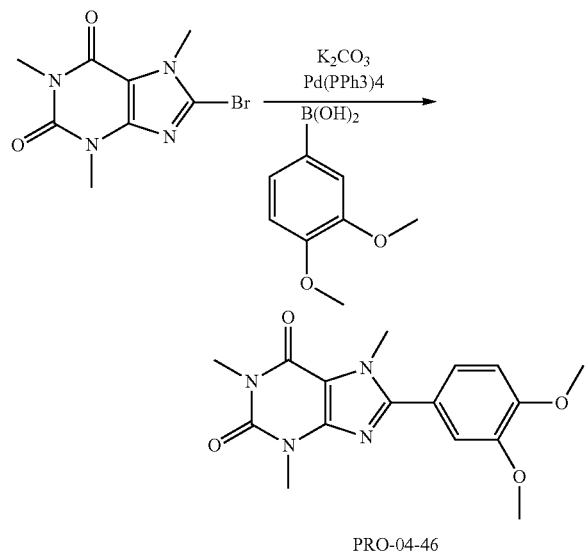

PRO-04-46

A solution of 8-Bromo-1,3,7-trimethyl xanthine (315 mg, 1.15 mmol) and 3,4-dimethoxy phenylboronic acid (230 mg; 1.26 mmol) in 1,4-dioxane (5 ml) was treated tetrakis(triphenyl phosphine) palladium (0) (88 mg, 0.14 mmol) and potassium carbonate (277 mg, 2.0 mmol). The mixture was heated to 70° C. for 12 hrs under argon atmosphere. The reaction mixture was concentrated under reduced pressure. The residue was purified on a silica gel column eluting with 70% ethyl acetate in hexane to 100% ethyl acetate. The desired product was isolated as off white solid, Yield 297 mg, 78% PRO-04-46

1,3,7-trimethyl-8-(3',4'-dihydroxyoxyphenyl)xanthine

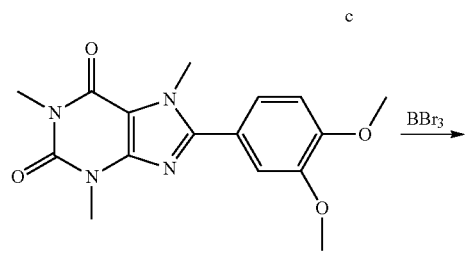

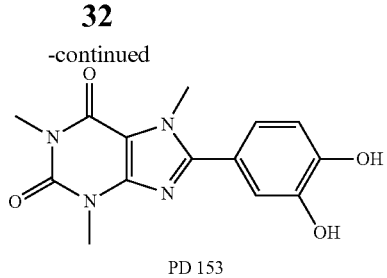

PD 153

Boron tribromide (1.62 g; 6.48 mmol) was added to a solution of 1,3,7-trimethyl-8-(3',4'-dimethoxyphenyl)xanthine (297 mg, 0.90 mmol) in anhydrous dichloromethane (12 ml) at −70° C. After 1 hr the reaction mixture was warmed to room temperature and stirred for 6 hr. Methanol (3 ml) was added and the reaction mixture was stirred overnight. The reaction mixture was concentrated under reduced pressure. The residue was purified on a silica gel column eluting with ethyl acetate. The desired product was isolated as off white solid, Yield 210 mg; 82% PD 153.

Example 2

Compounds Disrupt/Inhibit Pre-Aggregated Parkinson's Disease α-Synuclein Fibrils The compounds were found to be disrupters/disaggregators of α-synuclein fibrils. In this set of studies, the efficacy of certain compounds provided herein to cause a disassembly/disruption/disaggregation of pre-formed fibrils of Parkinson's disease (i.e. consisting of α-synuclein fibrils) was analyzed. For the studies described below in Parts A and B, 69 µM of α-synuclein (rPeptide, Bogart, Calif.) was first incubated at 37° C. for 4 days in 20 mM sodium acetate buffer at pH 4 with circular shaking (1,300 rpm) to cause α-synuclein aggregation and fibril formation.

Part A: Thioflavin T Fluorometry

In one study, Thioflavin T fluorometry was used to determine the effects of the compounds on α-synuclein fibrils. In addition to test compounds, this experiment included three control compounds (compounds 1, 2 and 3) for reference. In this assay Thioflavin T binds specifically to fibrillar protein, and this binding produces a fluorescence enhancement at 485 nm that is directly proportional to the amount of fibrils formed. The higher the fluorescence, the greater the amount of fibrils formed (Naki et al., Lab. Invest. 65:104-110, 1991; Levine III, Protein Sci. 2:404-410, 1993; Amyloid: Int. J. Exp. Clin. Invest. 2:1-6, 1995).

Following initial α-synuclein fibrilization as described above, the α-synuclein (6.9 µM) mixture was then incubated at 37° C. for 2 days with shaking (200 rpm), either alone, or in the presence of one of the compounds (at test compound:α-synuclein molar ratios of 10:1, 1:1, 0.1:1, and 0.01:1) in phosphate-buffered saline, pH 7.4+0.02% sodium azide. Following 2 days of co-incubation, 50 µl (5 µg) of each incubation mixture was transferred into a 96-well microtiter plate containing 150 µl of distilled water and 50 µl of a Thioflavin T solution (i.e. 500 µM Thioflavin T in 250 mM phosphate buffer, pH 6.8). The final concentration of Thioflavin T reagent is 100 µM in 50 mM phosphate buffer, pH 6.8. The fluorescence was read at 485 nm (444 nm excitation wavelength) using an ELISA plate fluorometer. Subtraction of the signal obtained from a diluted reaction (blank) containing buffer alone or compound alone at a concentration equivalent to that of its corresponding α-synuclein-containing reaction was used to quantitate the amount of Thioflavin T fluorescence in each α-synuclein-containing reaction that is proportional to the protein fibril content in that reaction.

The results of the 2-day incubations are presented below. For each compound, the % inhibition of Thioflavin T fluorescence is shown in Table 1. This study indicated that the compounds provided herein disrupt/disaggregate pre-formed Parkinson's disease α-synuclein fibrils.

TABLE 1

Compounds disrupt/disaggregate α-synuclein aggregates as measured by Thioflavin T fluorometry.

| Compound | Thioflavin T fluorometry-% Inhibition | | | |
|---|---|---|---|---|
| (molar ratios; compound:peptide) | 10:1 | 1:1 | 0.1:1 | 0.01:1 |
| Caffeine | 0 | 0 | 0 | 0 |
| PD-150 | 84 | 48 | 0 | 0 |
| PD-151 | 89 | 56 | 15 | 4 |
| PD-152 | 86 | 52 | 4 | 0 |
| PD-153 | 37 | 18 | 17 | 7 |
| PD-154 | 43 | 25 | 10 | 7 |
| Control 1 | 97 | 73 | 39 | 6 |
| Control 2 | 96 | 80 | 11 | — |
| Control 3 | 98 | 74 | 3 | — |

Part B: Congo Red Binding Data

In the Congo red binding assay, the ability of a given test compound to alter α-synuclein aggregate binding to Congo red is quantified. In this assay Congo red binds specifically to fibrillar protein, and this binding is directly proportional to the amount of fibrils formed. Following initial α-synuclein fibrilization as described above, α-synuclein aggregates and test compounds were incubated for 2 days and then vacuum filtered through a 0.2 μm filter. The amount of α-synuclein retained in the filter was then quantitated following staining of the filter with Congo red. After appropriate washing of the filter, any lowering of the Congo red color on the filter in the presence of the test compound (compared to the Congo red staining of the protein in the absence of the test compound—i.e. α-synuclein alone) was indicative of the test compound's ability to diminish/alter the amount of aggregated and congophilic α-synuclein and thus cause disassembly/disruption/disaggregation of α-synuclein fibrils.

In one study, the ability of α-synuclein fibrils to bind Congo red following a 2-day incubation of α-synuclein in the absence or presence of increasing amounts of the compounds provided herein, including positive reference (control) compounds (at test compound:α-synuclein molar ratios of 10:1, 1:1, 0.1:1, 0.01:1) was determined. The results of 2-day incubations are presented in Table 2 below. The results of this study indicate that compounds of this invention disrupt/disaggregate/disassemble pre-formed α-synuclein aggregates as indicated by their ability to inhibit Parkinson's disease type α-synuclein fibril binding to Congo red.

TABLE 2

Compounds disrupt/disaggregate α-synuclein fibrils/aggregates as measured by a Congo red binding assay.

| Compound (molar ratios; compound:peptide) | Congo Red Binding- % Inhibition 10:1 | | | |
|---|---|---|---|---|
| Caffeine | 0 | | | |
| PD-150 | 35 | 1:1 | 0.1:1 | 0.01:1 |
| PD-151 | 22 | 6 | 1 | 3 |
| PD-152 | 22 | 19 | 6 | 0 |
| PD-153 | 18 | 6 | 2 | 1 |

TABLE 2-continued

Compounds disrupt/disaggregate α-synuclein fibrils/aggregates as measured by a Congo red binding assay.

| Compound (molar ratios; compound:peptide) | Congo Red Binding- % Inhibition 10:1 | | | |
|---|---|---|---|---|
| PD-154 | 0 | 12 | 0 | 3 |
| Control 1 | 32 | 13 | 13 | 1 |
| Control 2 | 55 | 3 | 4 | 0 |
| Control 3 | 60 | 15 | 5 | 5 |

Example 3

Compounds Disrupt/Inhibit Freshly Dissolved Parkinson's Disease α-Synuclein Protein from Forming Fibrils (i.e. β-Sheet Secondary Structure)

Thioflavin T Fluorometry

To test whether the compounds can inhibit formation of α-synuclein β-sheet, the same assay as described in Example 2, was utilized but the α-synuclein was fresh and not pre-fibrillized. Fresh wild-type α-synuclein was dissolved in a buffer containing 9.5 mM phosphate, 137 mM sodium chloride and 2.7 mM potassium chloride (phosphate-buffered saline; PBS), and the pH was adjusted to pH 7.4. This solution was then lyophilized and dissolved in 1.0 ml deionized water at 0.5 mg/ml (35 μM). As indicated above the test compounds (typically at test compound:α-synuclein molar ratios of 10:1, 1:1, 0.1:1, and 0.01:1) were then added to the α-synuclein. Following 24-38 hours of co-incubation, the incubation mixtures were diluted 1:10 and 50 μl of each diluted incubation mixture was transferred into a 96-well microtiter plate containing 150 μl of distilled water and 50 μl of a Thioflavin T solution (i.e. 500 μM Thioflavin T in 250 mM phosphate buffer, pH 6.8). The final concentration of α-synuclein was 0.7 μM and the concentration of Thioflavin T reagent was 100 μM in 50 mM phosphate buffer, pH 6.8. In some experiments, 200 μl of each diluted incubation mixture was combined in the 96-well microtiter plate with 50 μl of the 500 μM Thioflavin T solution to give 2.8 μM α-synuclein in the presence of 100 μM Thioflavin T reagent. The fluorescence was read at 485 nm (444 nm excitation wavelength) using an ELISA plate fluorometer after subtraction with buffer alone or compound alone, as blank. Positive control compound 1 performed nearly identically in inhibiting α-synuclein aggregation regardless of whether 0.7 μM or 2.8 μM α-synuclein was subsequently used in the Thioflavin T reaction.

The complete results of this study presented in Table 3 indicated that compounds of this invention interfered with α-synuclein aggregation as indicated by their ability to prevent the formation of α-synuclein β-sheet secondary folding as assessed by Thioflavin T fluorometry.

TABLE 3

Compounds inhibit formation of α-synuclein β-sheet-rich structures as measured by Thioflavin T Fluorometry

| Compound | ThioT Assay % Inhibition | | | |
|---|---|---|---|---|
| (molar ratio; compound:peptide) | 10:1 | 1:1 | 0.1:1 | 0.01:1 |
| Caffeine | 0 | 0 | 0 | 0 |
| PD-150 | 91 | 22 | 0 | 0 |
| PD-151 | 78 | 0 | 0 | 0 |

TABLE 3-continued

Compounds inhibit formation of α-synuclein β-sheet-rich structures as measured by Thioflavin T Fluorometry

| Compound | ThioT Assay % Inhibition | | | |
|---|---|---|---|---|
| (molar ratio; compound:peptide) | 10:1 | 1:1 | 0.1:1 | 0.01:1 |
| PD-152 | 72 | 0 | 0 | 0 |
| PD-153 | 80 | 0 | 23 | 13 |
| PD-154 | 89 | 89 | 44 | 8 |
| Control 1 | — | 100 | 100 | 0 |

Example 4

Compounds of this Invention are Potent Disruptors/Inhibitors of α-Synuclein Fibrils and/or Aggregates Associated with Parkinson's Disease Parkinson's Disease is characterized by the accumulation of insoluble intraneuronal aggregates called Lewy Bodies, a major component of which is α-synuclein (reviewed in Dauer et al., *Neuron*, 39:889-909, 2003). Since autosomal dominant mutations in α-synuclein cause a subset of familial Parkinson's disease, and since these mutations increase the likelihood of α-synuclein to aggregate and form Lewy Bodies, aggregated α-synuclein is proposed to be directly involved in the etiology and disease progression (Polymeropoulos et al., *Science* 276:1197-1199, 1997; Papadimitriou et al., *Neurology* 52:651-654, 1999). Structural studies have revealed that intracellular Lewy bodies contain a large proportion of misfolded proteins with a high degree of β-pleated sheet secondary structure. Therefore, since many of the compounds described herein cause disassembly/disruption/disaggregation of α-synuclein aggregates in the in vitro assays (Thioflavin T fluorometry and Congo Red binding assays) described above, studies were also conducted in living cells to determine the efficacy of these compounds to inhibit or prevent α-synuclein aggregation associated with Parkinson's disease.

To test the therapeutic potential of the compounds, a cell-based assay was utilized. In this assay, rotenone is used to induce mitochondrial oxidative stress and cause α-synuclein aggregation. The assay utilizes the binding of the fluorescent dye Thioflavin S to structures with high β-sheet content, including α-synuclein fibrils. Therefore, quantitative assessment of the extent of Thioflavin S-positive staining of fixed cells is used to test the ability of the test compounds to inhibit/prevent or decrease the amount of α-synuclein aggregates relative to cells that were treated with rotenone only. This study is presented in the following examples.

To carry out these studies, a cell culture model was used in which human α-synuclein aggregation is experimentally induced. BE-M17 human neuroblastoma cells stably transfected with A53T-mutant human α-synuclein were obtained. Cell culture reagents were obtained from Gibco/Invitrogen, and cells were grown in OPTIMEM supplemented with 10% FBS, Penicillin (100 units/ml), Streptomycin (100 µg/ml) and 500 µg/ml G418 as previously described (Ostrerova-Golts et al., *J. Neurosci.*, 20:6048-6054, 2000).

Thioflavin S is commonly used to detect aggregated protein structures in situ, including in brain tissue (Vallet et al., *Acta Neuropathol.*, 83:170-178, 1992), and cultured cells (Ostrerova-Golts et al., *J. Neurosci.*, 20:6048-6054, 2000), whereas Thioflavin T is often used as an in vitro reagent to analyze the aggregation of soluble proteins into fibrils enriched in β-pleated sheet structures (LeVine III, *Prot. Sci.*, 2:404-410, 1993). Therefore, Thioflavin S histochemistry was used on cultured cells to detect aggregates containing a high degree of β-pleated structures that formed in response to oxidative stress-inducing agents (in this case rotenone) as previously described, with minor modifications (Ostrerova-Golts et al., *J. Neurosci.*, 20:6048-6054, 2000). Briefly, for these studies cells were grown on Poly-D-Lysine coated glass slide chambers at approximately $4.5-5.5 \times 10^4$ cells/cm$^2$. After 16-18 hours, cells were treated with 500 nM or 2 µM rotenone (Sigma) or vehicle (0.05% DMSO) as indicated. Within 15 minutes of rotenone (or vehicle) addition, compounds were added at the indicated concentration, or mock-treatment was performed in which cell culture media only (no compound) was added. Identical treatments were repeated after 48 hours. After an additional 24 hours, cells were fixed for 25 minutes in 3% paraformaldehyde. After a PBS wash and a deionized water wash, the cells were incubated with 0.015% Thioflavin S in 50% ethanol for 25 minutes, washed twice for four minutes in 50% ethanol and twice for five minutes in deionized water and then mounted using an aqueous-based mountant designed to protect against photobleaching. Aggregates that bind to Thioflavin S were detected with a fluorescent microscope using a High Q FITC filter set (480 to 535 nm bandwidth) and a 20× objective lens unless otherwise indicated. Between 8 and 20 (usually 16-18) representative images per condition were selected and imaged using Q Capture software by an experimenter who was blinded to treatment conditions. To assess the amount of Thioflavin S-positive aggregates, the total area per field covered by Thioflavin S-positive inclusions was determined by image analysis and quantitation. For this purpose, background fluorescence that failed to exceed pre-set size or pixel intensity threshold parameters was eliminated using Image Pro Plus software. Spurious, non-cell associated fluorescence was manually removed. Unless indicated otherwise, comparisons between groups were made by comparing mean relative amounts of Thioflavin S-positive inclusions for a given treatment condition (i.e. cells treated with rotenone only versus cells treated with rotenone and test compound at a given concentration). Statistical analyses were performed with GraphPad Prism (GraphPad Inc). Differences between means (two samples) were assessed by the Student's t test. Differences among multiple means were assessed by one-factor ANOVA followed by Dunnett's post hoc test, compared to rotenone only treated cells. The data presented below represent statistically significant (p<0.05) reductions (reported as percent inhibition) in Thioflavin S fluorescence in cells treated with test compound and rotenone relative to cells treated with rotenone only.

To validate the ability of the assay to quantitatively detect aggregates that bind Thioflavin S, staining of BE-M17 cells overexpressing A53T α-synuclein was carried out and the results revealed a rotenone dose-dependent increase in Thioflavin S-positive aggregates relative to vehicle-treated control cells (not shown). Higher magnification images obtained with a 40× objective indicated that the Thioflavin S-positive aggregates were intracellular and cytoplasmic, analogous to the accumulation of intracytoplasmic Lewy bodies that are pathological hallmarks associated with Parkinson's disease (not shown). Quantitation of the area covered by Thioflavin-S-positive aggregates established that 500 nM and 2 µM rotenone were sufficient to induce robust aggregation (not shown) and thus are effective doses to test the ability of compounds to attenuate the formation of these aggregates.

Using the protocol described above, selected compounds were tested for their ability to reduce, inhibit, prevent or eliminate Thioflavin S-positive aggregates in rotenone-treated BE-M17 cells overexpressing A53T α-synuclein. Some of the compounds tested significantly disrupted, prevented or inhibited α-synuclein aggregation and fibril formation in the presence of rotenone as indicated by a decrease in Thioflavin S-positive inclusions, relative to cells treated with rotenone only. For example, cells treated only with 500 nM rotenone exhibited a robust presence of Thioflavin S-positive aggregates, whereas addition of 500 nM or 2 μM PD-151 markedly reduced the abundance of these rotenone-induced aggregates by 52% and 84%, respectively, relative to rotenone only-treated cells. Similarly, in cells treated only with 2 μM rotenone, there was a robust presence of Thioflavin S-positive aggregates, whereas addition of 2 μM or 5 μM PD-151 markedly reduced the abundance of these rotenone-induced aggregates by 58% and 60%, respectively, relative to rotenone only-treated cells. Therefore, PD-151 reduced, inhibited, prevented and/or eliminated Thioflavin S-positive aggregates in cells that express human A53T α-synuclein.

In addition, PD-152, at given concentrations, showed significant disruption/prevention/inhibition of rotenone-induced Thioflavin S-positive inclusions when tested in a similar fashion. For example, cells treated only with 500 nM rotenone exhibited a robust presence of Thioflavin S-positive aggregates, whereas addition of 2 μM or 5 μM PD-152 markedly reduced the abundance of these rotenone-induced aggregates by 54% and 55%, respectively, relative to rotenone only-treated cells. Similarly, in cells treated only with 2 μM rotenone, there was a robust presence of Thioflavin S-positive aggregates, whereas addition of 500 nM or 2 μM PD-152 markedly reduced the abundance of these rotenone-induced aggregates by 78% and 79%, respectively, relative to rotenone only-treated cells. Therefore, PD-152 also reduced, inhibited, prevented and/or eliminated Thioflavin S-positive aggregates in cells that express human A53T α-synuclein.

Taken together, we concluded that the tested compounds PD-151 and PD-152 effectively and potently reduced, prevented and/or inhibited the formation, deposition and/or accumulation of α-synuclein aggregates in A53T α-synuclein-expressing BE-M17 cells.

Example 5

Compounds of this Invention are Potent Disrupters/Inhibitors of Alzheimer's Aβ1-42 Fibrils or Aggregates The compounds prepared in the preceding Examples were found to be potent disruptors/inhibitors of Parkinson's disease α-synuclein protein fibrils or aggregates. In a set of studies, the efficacy of the compounds to cause a disassembly/disruption/disaggregation of pre-formed amyloid fibrils of Alzheimer's disease (i.e. consisting of Aβ 1-42 fibrils) was analyzed.

Part A—Thioflavin T Fluorometry

In one study, Thioflavin T fluorometry was used to determine the effects of the compounds, and of caffeine (as a negative control). In this assay Thioflavin T binds specifically to fibrillar amyloid, and this binding produces a fluorescence enhancement at 485 nm that is directly proportional to the amount of amyloid fibrils formed. The higher the fluorescence, the greater the amount of amyloid fibrils formed (Naki et al., *Lab. Invest.* 65:104-110, 1991; Levine III, *Protein Sci.* 2:404-410, 1993; *Amyloid: Int. J. Exp. Clin. Invest.* 2:1-6, 1995).

In this study, 30 μL of a 1 mg/mL solution (in distilled water) of pre-fibrillized human Aβ 1-42 (rPeptide) was incubated at 37° C. for 2 days either alone, or in the presence of one of the compounds or caffeine (at test compound:Aβ molar ratios of 10:1, 5:1, 1:1, 0.1:1 or 0.05:1). The final concentration of Aβ in the reaction is 0.1 mg/mL (22 μM) in phosphate-buffered saline, pH 7.4+0.02% sodium azide in 300 μL final volume. Following 2-days of co-incubation, 50 μL of each incubation mixture was transferred into a 96-well microtiter plate containing 150 μL of distilled water and 50 μL of a Thioflavin T solution (i.e. 500 μM Thioflavin T in 250 mM phosphate buffer, pH 6.8). The emission fluorescence was read at 485 nm (444 nm excitation wavelength) using an ELISA plate fluorometer after subtraction with buffer alone or compound alone, as blank.

The results of the 2-day incubations are presented in Table 4. For example, whereas caffeine caused no significant inhibition of Aβ 1-42 fibrils at all concentrations tested, the compounds all caused a dose-dependent disruption/disassembly/disaggregation of preformed Aβ 1-42 fibrils. All of the compounds tested were effective in disrupting pre-formed Aβ 1-42 fibrils. These results are similar to the results obtained from a positive control compound (not shown) that demonstrated robust inhibition of Thioflavin T fluorescence. For example, all of the compounds in this invention caused at least 63% inhibition of Thioflavin T fluorescence when used at a test compound:Aβ:molar ratio of 10:1. At a test compound:Aβ molar ratio of 5:1 the levels of inhibition ranged from 17 to 87% and all compounds except PD-153 showed at least 74% inhibition at this 5:1 (test compound:Aβ) concentration. Even at equimolar concentrations (test compound:Aβ molar ratio of 1:1) there was at least 54% inhibition of Thioflavin T fluorescence for all compounds except PD-153. Interestingly, PD-150 and PD-154 were effective against Aβ fibrils/aggregates at substoichiometric concentrations (i.e. test compound:Aβ molar ratios of 0.1:1 and 0.05:1) in this assay. This study indicated that the compounds of this invention are potent disruptors/inhibitors of Alzheimer's disease type Aβ fibrils, and usually exert their effects in a dose-dependent manner.

TABLE 4

Compounds disrupt/disaggregate Aβ fibrils/aggregates as measured by a Thioflavin T fluorometry assay.

| Compound | Thioflavin T fluorometry % Inhibition | | | | |
|---|---|---|---|---|---|
| (molar ratios; compound:peptide) | 10:1 | 5:1 | 1:1 | 0.1:1 | 0.05:1 |
| Caffeine | 8 | 0 | 0 | — | — |
| PD-150 | 94 | 87 | 67 | 35 | 41 |
| PD-151 | 94 | 87 | 56 | 20 | 18 |
| PD-152 | 91 | 87 | 54 | 13 | 12 |
| PD-153 | 63 | 17 | 6 | 0 | 5 |
| PD-154 | 80 | 74 | 60 | 36 | 43 |

Part B: Congo Red

In the Congo red binding assay the ability of a test compound to alter β-amyloid binding to Congo red is quantified. In this assay, Aβ 1-42 (as prepared for the Thio T assay) and test compounds were incubated for 2 days and then vacuum filtered through a 0.2 μm filter. The amount of Aβ 1-42 retained in the filter was then quantitated following staining of the filter with Congo red. After appropriate washing of the filter, any lowering of the Congo red color on the filter in the presence of the test compound (compared to the Congo red staining of the amyloid protein in the absence of the test compound) was indicative of the test compound's ability to diminish/alter the amount of aggregated and congophilic Aβ.

In one study, the ability of Aβ fibrils to bind Congo red in the absence or presence of increasing amounts of the compounds or caffeine (at test compound:Aβ molar ratios of 10:1, 5:1, 1:1, or 0.1:1) was determined. The results of 2-day incubations are presented in Table 5. Whereas caffeine caused no significant inhibition of Aβ 1-42 fibril binding to Congo red at all concentrations tested, the compounds caused a dose-dependent inhibition of Aβ binding to Congo red. For example, PD-150, PD-151 and PD-152 each caused a significant inhibition (ranging from 59-63% inhibition) of Congo red binding to Aβ 1-42 fibrils when used at a test compound:Aβ molar ratio of 10:1, and a significant inhibition of Congo red binding when used at a test compound:Aβ molar ratio of 5:1 (ranging from 46-48% inhibition). Similar to the results for the Thioflavin T fluorometry assay, this study also indicated that compounds of this invention are potent disruptors/inhibitors of Aβ fibrils as assessed by Aβ fibril binding to Congo red, and usually exert their effects in a dose-dependent manner.

TABLE 5

Compounds disrupt/disaggregate Aβ fibrils/aggregates as measured by a Congo Red binding assay.

| Compound | Congo Red Binding % Inhibition | | | |
|---|---|---|---|---|
| (molar ratios; compound:peptide) | 10:1 | 5:1 | 1:1 | 0.1:1 |
| Caffeine | 1 | 0 | 0 | — |
| PD-150 | 60 | 46 | 18 | 10 |
| PD-151 | 63 | 47 | 12 | 13 |
| PD-152 | 59 | 48 | 21 | 4 |
| PD-153 | 20 | 19 | 20 | 7 |
| PD-154 | 0 | 0 | 0 | 0 |

Example 6

Compounds of this Invention Directly Inhibit/Disrupt the In Vitro Conversion of Aβ to β-Sheet Containing Fibril Structures Part A: Thioflavin T Fluorometry To test whether the compounds can inhibit β-sheet formation of Aβ, the same assay as described in Example 5 was utilized, but the Aβ was prepared so that it is in a non-fibrillar state at the start of the assay. To achieve this non-fibrillar state, lyophilized human Aβ 1-42 (rPeptide) was dissolved to 1 mg/mL (220 μM) using 2 mM NaOH and the pH was adjusted to 10.5 with small (μL) additions of 1M NaOH. The clear solution was then frozen, re-lyophilized, and dissolved in a buffer containing 9.5 mM phosphate, 137 mM sodium chloride and 2.7 mM potassium chloride (phosphate-buffered saline; PBS) to a concentration of 2 mg/mL (440 μM) Aβ. In separate tubes, test compound stocks were prepared in PBS at various concentrations such that final reactions containing equal volumes of the test compound stocks and the Aβ solution would result in a final Aβ concentration of 1 mg/mL (220 μM) with test compound:Aβ molar ratios of 10:1, 5:1, 1:1, and 0.5:1. The reactions containing Aβ+test compounds (or Aβ+PBS as a control for Aβ aggregation) were then incubated for 24 hours, the incubation mixtures were diluted 1:20 to 0.05 mg/mL Aβ and 50 μL of each diluted incubation mixture was transferred into a 96-well microtiter plate containing 150 μL of distilled water and 50 μL of a Thioflavin T solution (i.e. 500 μM Thioflavin T in 250 mM phosphate buffer, pH 6.8). The final concentration of Aβ was 2.2 μM and the concentration of Thioflavin T reagent was 100 μM in 50 mM phosphate buffer, pH 6.8. The fluorescence was read at 485 nm (444 nm excitation wavelength) using an ELISA plate fluorometer after subtraction with PBS buffer alone or compound alone, as blank.

The complete results of this study presented in Table 6 indicated that compounds of this invention interfered with Aβ aggregation as indicated by their ability to prevent the formation of β-sheet secondary folding of Aβ as assessed by Thioflavin T fluorometry. For example, PD-150, PD-151 and PD-152 each caused a significant inhibition (ranging from 61-93% inhibition) of Thioflavin T fluorescence when used at a test compound:Aβ molar ratio of 10:1, and a significant inhibition of Thioflavin T fluorescence when used at a test compound:Aβ molar ratio of 5:1 (ranging from 23-87% inhibition). The positive control compound (Control 4) performed as expected and completely inhibited Aβ aggregation (by 100%) at test compound:Aβ molar ratios 1:1 whereas the negative control compound (caffeine) failed to inhibit Aβ aggregation at any of the concentrations tested (50:1, 10:1 and 1:1). This study indicated that compounds of this invention are potent inhibitors of β-sheet rich-Aβ fibril formation as assessed by Thioflavin T fluorometry, and the compounds usually exert their effects in a dose-dependent manner.

TABLE 6

Compounds inhibit formation of β-sheet-rich structures of Aβ as measured by Thioflavin T Fluorometry.

| Compound | Thioflavin T fluorometry - % Inhibition | | | |
|---|---|---|---|---|
| (molar ratios; compound:Aβ) | 10:1 | 5:1 | 1:1 | 0.5:1 |
| Control 4 | 100 | 100 | 100 | 76 |
| Caffeine | — | — | — | — |
| PD-150 | 93 | 87 | 23 | — |
| PD-151 | 87 | 79 | 9 | — |
| PD-152 | 61 | 23 | — | — |
| PD-153 | — | — | — | — |
| PD-154 | 33 | 0 | — | — |

Part B: Circular Dichroism (CD) Spectroscopy

Since several compounds were shown to reduce the abundance of Thioflavin T-positive aggregates (Table 6), we sought independent confirmation that the compounds directly inhibit the conversion of Aβ to β-sheet containing structures by using circular dichroism (CD) spectroscopy. For this purpose, the Aβ reactions that were used in the Thioflavin T fluorometry assay (Part A in this Example) were assessed at 24 hours of aggregation. Aβ alone was also assessed by CD spectral analysis at t=0, prior to aggregation, (t=0, unfolded reference control). After 24 hours, reactions were diluted 20-fold in PBS and a CD spectrum for each reaction was acquired on a Jasco J-810 spectropolarimeter using a 0.1 cm path length cell. All spectra were recorded with a step size of 0.1 nm, a bandwidth of 1 nm, and an Aβ concentration of 0.05 mg/ml. The spectra were trimmed at the shortest wavelength that still provided a dynode voltage less than 600V. The trimmed spectra were then subjected to a data processing routine beginning with noise reduction by Fourier transform followed by subtraction of a blank spectrum (vehicle only without Aβ). These blank corrected spectra were then zeroed at 260 nm and the units converted from millidegrees to specific ellipticity.

Percent β-sheet was determined from processed spectra using the ellipticity minimum value at approximately 218 nm and referencing to a scale normalized to nearly fully folded and unfolded reference values, consistent with previous reports (Ramirez-Alvarado et al., *J. Mol. Biol.*, 273:898-912, 1997; Andersen et al., *J. Am. Chem. Soc.*, 121:9879-9880, 1999). The fully folded reference value was found by performing the described calculation on the spectrum of Aβ fibrillized for 24 hours (complete fibrillization), and assigning this difference the arbitrary value of 100% β-sheet. The unfolded reference was provided by the spectrum from the same sample at the initial time point (t=0) and ascribing the difference found here the arbitrary value of 0% β-sheet. These percent β-sheet values were then used to provide the respective relative % inhibition of β-sheet induced by the compounds at given molar ratio of test compound:Aβ.

First, in order to confirm that Aβ 1-42 is indeed converted to a β-sheet-rich structure and to establish the timing of this conversion at 24 hours in our system, an aliquot of the Aβ only incubation mixture (without compounds) was sampled and the CD spectrum was collected. At 24 hours of incubation, CD analysis revealed a large abundance of a β-sheet-rich structure(s), indicated by the pronounced specific ellipticity minimum at 218 nm and maximum at 197 nm (not shown). However, when test compounds PD-150, PD-151, PD-152, PD-153 or the positive control compound (control 4) were included individually in the reaction mixture, at appropriate concentrations, at 24 hours of incubation the magnitude of the change of the minimum at 218 nm was reduced, relative to Aβ alone, and the spectra were more characteristic of random coil structure. Thus, we conclude that some of the compounds in this invention inhibit, to varying degrees, the conversion of natively unfolded Aβ to a β-sheet-rich structure. On the other hand, the negative control compound, caffeine, had no effect on the magnitude of change in the ellipticity minima at 218 nm. These results are summarized in Table 7. As a specific example of a test compound that inhibits β-sheet formation in Aβ, compound PD-150 resulted in at least 62% inhibition when used at test compound:Aβ molar ratios≥5:1. Taken together, these results indicate that some of the compounds in this invention show potent inhibition and prevention of Aβ aggregation, a hallmark of the amyloid diseases such as Alzheimer's disease.

TABLE 7

Compounds inhibit formation of β-sheet-rich structures of Aβ as measured by Circular Dichroism (CD) Spectroscopy

| Compound | Circular Dichroism Spectroscopy -% Inhibition | | | |
|---|---|---|---|---|
| (molar ratios; compound:Aβ) | 10:1 | 5:1 | 1:1 | 0.5:1 |
| Control 4 | 59 | 63 | 64 | 21 |
| Caffeine | — | — | — | — |
| PD-150 | 62 | 69 | 42 | 40 |
| PD-151 | 67 | 66 | 43 | 38 |
| PD-152 | 57 | 35 | 42 | 26 |
| PD-153 | 24 | 8 | — | — |
| PD-154 | — | — | — | — |

Example 7

Compounds of this Invention Display Therapeutically Relevant Levels in Plasma and Brain Consistent with a Drug Intended for Treatment of Central Nervous System Disorders For select compounds in this invention, we have used wild type mice to determine the following plasma pharmacokinetic (PK) parameters: maximal concentration ($C_{max}$), and area under the curve (AUC) as derived from a time versus concentration plot. We have also determined the maximal mouse brain levels, and overall brain exposure over time of select compounds in this invention, expressed as $C_{max}$-brain and AUC-brain, respectively. In order to establish the method, we assessed brain and plasma compound levels over time utilizing 50 mg/kg intraperitoneal (i.p.) injections of 2 control compounds. These results indicated a rapid spike in plasma levels and brain uptake of these control compounds, followed by complete clearance from blood by 6 hours post-dose (data not shown). In a typical experiment to assess the compounds in this invention, we used CD-1 female mice with a sample size (n) equal to 4 mice per post-dose time-point (for example, 7, 15, 30, and 60 min post-dose). We chose early time points to assess initial exposure, when we expected plasma and brain exposure to be the high, though we may have missed even higher exposure at earlier time points (between 0 and 7 minutes) since brain and plasma levels were highest in our study at the earliest time point assessed (7 minutes).

For the purpose of these studies, each compound was formulated at 5 mg/mL in 20% polyethylene glycol (PEG)-400 in PBS+0.1% ascorbic acid (w/v). The dose volume was 10 mL/kg of body weight. Mice were administered test compound via intraperitoneal injection, and at about 2-3 minutes before scheduled sacrifice, they were deeply anesthetized with 2.5% avertin. Once anesthetized, whole blood was removed by cardiac puncture, transferred to appropriate EDTA-containing tubes, and immediately chilled on ice. This was followed by complete perfusion of each mouse with >15 ml cold 0.9% saline by cannulation of the left ventricle and clamping of the descending aorta. Brains were harvested, frozen on dry ice and stored at −80° C. for bioanalysis of the test compound. Plasma was extracted from whole blood by standard centrifugation techniques within 1 hour. Compounds were (liquid-liquid) extracted from plasma and brain homogenates using ethyl acetate, followed by HPLC/MS quantitation using methods (i.e. HPLC gradients and mass spectrometry parameters) developed for these novel compounds. All methods established sufficient stability in relevant matrices and solvents, and used internal quantitation controls. Quantitation was achieved using a calibration curve generated with compounds spiked into the appropriate matrix (i.e. 20% PEG-400/PBS+0.1% ascorbic acid). We have established lower limit of quantitative sensitivities of 5-25 ng/ml (plasma) and 5-25 ng/g (brain), sufficient for these studies. Following determination of the brain and plasma concentrations at the various post-dose time points, select plasma ($C_{max}$ and AUC) and brain ($C_{max}$-brain and AUC-brain) PK parameters were determined with WinNonLin software (Pharsight Inc). We compared the values determined for the compounds in this invention to the values for the positive control compound that when administered at the same therapeutically relevant route and dose level (i.p. injection at 50 mg/kg) is known to be present in the plasma and the brain at levels sufficient for a biological effect (i.e. reduction of α-synuclein brain levels and improved motor function; data not shown).

Using the protocol described above, for example, we determined that PD-151 has a plasma $C_{max}$=5,340 ng/mL and plasma AUC=212,417 min*ng/mL. This plasma exposure compares favorably with the positive control compound that has a plasma $C_{max}$=8,230 ng/mL and plasma AUC=420,406. In brain, PD-151 has a $C_{max}$-brain=59.2 ng/g and AUC-brain=2,147 min*ng/g. This brain exposure compares favorably with the positive control compound that has a $C_{max}$-brain=94.6 ng/g and AUC-brain=7,029 min*ng/g. PD-150 also showed acceptable plasma and brain exposure. For example, PD-150 has a plasma $C_{max}$=3,284 ng/mL, plasma AUC=127,662 min*ng/mL, $C_{max}$-brain=99.5 ng/g and AUC-brain=3,048 min*ng/g.

Taken together, these results indicate that some of the compounds in this invention are shown to have plasma and brain exposure that is consistent with a drug intended to treat a central nervous system disorder such as Alzheimer's or Parkinson's disease where the primary target is a brain protein. For example, the levels of the compounds in this invention have a brain and plasma exposure that is comparable to a control compound (i.e. no greater than 3.3-fold different than the control compound) when that control compound is administered at a therapeutically effective amount in a disease-relevant animal model.

We claim:

1. A compound selected from the group consisting of compounds of the formula

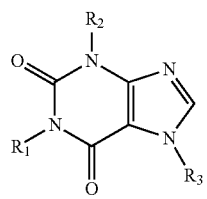

where:

$R_{1-3}$ are independently substituted with hydrogen, methyl and benzyl groups, wherein at least two of $R_{1-3}$ are benzyl substituted at any one time, and wherein the benzyl groups are substituted with two hydroxy groups, and pharmaceutically acceptable salts thereof.

2. The compound a claim 1 selected from the group consisting of:

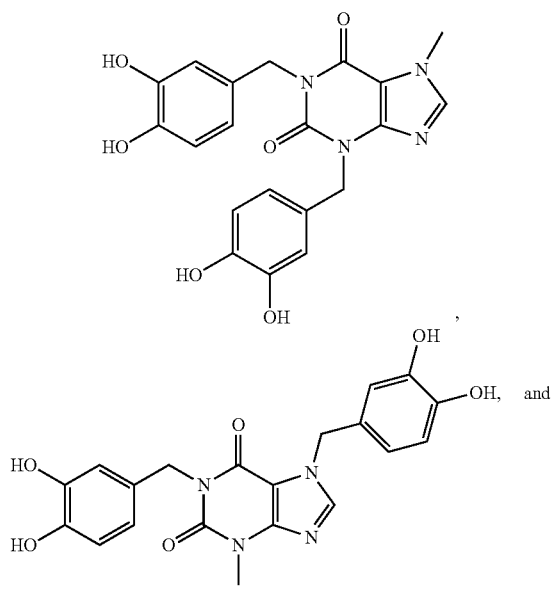

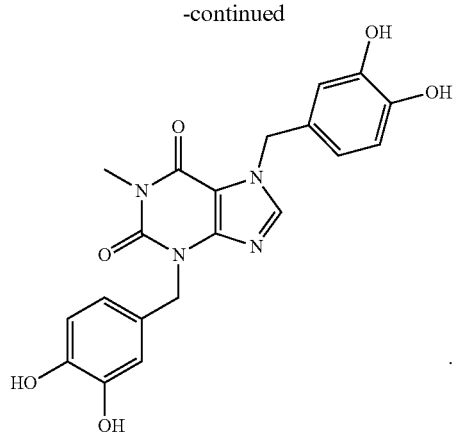

3. A pharmaceutical composition comprising the compound of claim 1 and a pharmaceutically acceptable excipient.

4. A method of treating the formation, deposition, accumulation, or persistence of amyloid or α-synuclein fibrils, comprising treating the fibrils with an effective amount of the compound of claim 1.

5. A method of inhibiting the formation, deposition, accumulation, or persistence of amyloid or α-synuclein fibrils in a mammal suffering from an amyloid disease or a synucleinopathy, comprising administration of a therapeutically effective amount of the compound of claim 1.

6. The method of claim 5 where the amyloid disease is selected from the group of diseases consisting of Alzheimer's disease, type II diabetes, systemic AA amyloidosis, Down's syndrome, hereditary cerebral hemorrhage with amyloidosis of the Dutch type, and cerebral β-amyloid angiopathy.

7. The method of claim 5 where the amyloid disease is Alzheimer's disease.

8. The method of claim 5 where the synucleinopathy is selected from the group consisting of Parkinson's disease, familial Parkinson's disease, Lewy body disease, the Lewy body variant of Alzheimer's disease, dementia with Lewy bodies, multiple system atrophy, and the Parkinsonism-dementia complex of Guam.

9. The method of claim 5 where the synucleinopathy is Parkinson's disease.

10. The method of claim 5, where the compound administered is in an amount between 0.1 mg/Kg/day and 1000 mg/Kg/day.

11. The method of claim 5, where the compound is administered in an amount between 1 mg/Kg/day and 100 mg/Kg/day.

12. The Method of claim 5, where the compound administered is in an amount between 10 mg/Kg/day and 100 mg/Kg/day.

13. An article of manufacture, comprising packaging material, the compound of claim 1, or a pharmaceutically acceptable salt thereof, contained within packaging material, which is used for treating the formation, deposition, accumulation, or persistence of β-amyloid or α-synuclein and/or aggregates, and a label that indicates that the compound or pharmaceutically acceptable salt thereof is used for treating the formation, deposition, accumulation, or persistence of β-amyloid or α-synuclein fibrils and/or aggregates.

* * * * *